United States Patent [19]
Sato et al.

[11] Patent Number: 5,763,475
[45] Date of Patent: Jun. 9, 1998

[54] METHOD OF CONTROL PLANT DISEASE

[75] Inventors: Junichi Sato, Toyonaka; Tadashi Ohsumi, Nishinomiya; Hiroko Yamazaki; Norio Kimura, both of Takarazuka; Hirotaka Takano, Sanda; Makoto Fujimura, Toyonaka; Noriko Ohsawa, Sakai, all of Japan

[73] Assignee: Sumitomo Chemical Co., Ltd., Osaka, Japan

[21] Appl. No.: 743,625

[22] Filed: Nov. 4, 1996

Related U.S. Application Data

[63] Continuation of Ser. No. 409,080, Mar. 22, 1995, abandoned.

[30] Foreign Application Priority Data

Mar. 30, 1994 [JP] Japan .................. 6-0610018
Dec. 1, 1994 [JP] Japan .................. 6-298337

[51] Int. Cl.$^6$ .................. A01N 43/56
[52] U.S. Cl. .................. 514/404; 514/407; 548/368.7
[58] Field of Search .................. 514/404, 407

[56] References Cited

U.S. PATENT DOCUMENTS

| | | |
|---|---|---|
| 4,772,608 | 9/1988 | Sasse et al. . |
| 4,806,540 | 2/1989 | Sasse et al. . |
| 4,909,830 | 3/1990 | Jensen-Korte et al. . |
| 5,332,720 | 7/1994 | Kruger et al. . |
| 5,358,924 | 10/1994 | Kruger et al. . |

FOREIGN PATENT DOCUMENTS

| | | |
|---|---|---|
| B4256585 | 11/1985 | Australia . |
| B2505988 | 5/1989 | Australia . |
| 0165448 | 12/1985 | European Pat. Off. . |
| 0212281 | 3/1987 | European Pat. Off. . |
| 0316733 | 5/1989 | European Pat. Off. . |
| 0508126 | 10/1992 | European Pat. Off. . |
| 1160968 | 6/1989 | Japan ............ C07D 231/52 |
| 01971 | 1/1995 | WIPO . |
| WO 9501971 | 1/1995 | WIPO . |
| WO 9501973 | 1/1995 | WIPO . |

OTHER PUBLICATIONS

Tetrahedron Letters, vol. 31, No. 37, pp. 5327–5330, 1990.
J. Agric. Food Chem., 1990, 38, pp. 1601–1603.

*Primary Examiner*—Robert W. Ramsuer
*Attorney, Agent, or Firm*—Sughrue, Mion, Zinn, Macpeak & Seas, PLLC

[57] ABSTRACT

A plant disease-controlling agent containing as an effective ingredient a pyrazoline derivative represented by the general formula

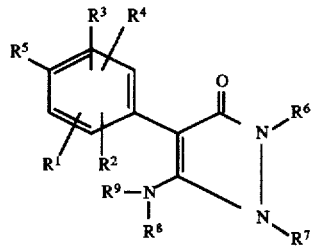

wherein, $R^1$ to $R^4$ denote hydrogen atoms, etc., $R^5$ denotes a hydrogen atom, etc., $R^6$ and $R^7$ are the same or different and denote optionally substituted hydrocarbon groups, and $R^8$ and $R^9$ are the same or different and denote hydrogen atoms, etc., provided that not all of $R^1$ to $R^5$ denote hydrogen atoms at the same time.

The pyrazoline derivatives represented by the above general formula exhibit excellent control effects on plant diseases.

6 Claims, No Drawings

METHOD OF CONTROL PLANT DISEASE

This is a Continuation of application Ser. No. 08/409,080 filed Mar. 22, 1995 now abandoned.

BACKGROUND OF THE INVENTION

Field of the Invention

This invention relates to a plant disease-controlling agent.

SUMMARY OF THE INVENTION

The present inventors had made intensive study, for developing an excellent plant disease-controlling agents, and as a result they found that pyrazoline derivatives represented by the following general formula I, particularly pyrazoline derivatives represented by the following general formula II, have excellent control effects on plant diseases, and completed this invention. Namely, this invention provides a plant disease-controlling agent containing as an effective ingredient a pyrazoline derivative represented by the general formula I

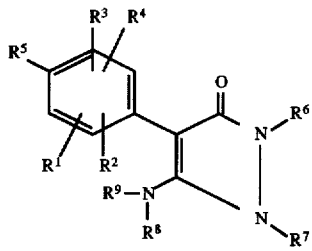

wherein, $R^1$ to $R^4$ each denote a hydrogen atom, a halogen atom, an alkyl group, a haloalkyl group, an alkoxy group, an alkoxyalkoxy group, a haloalkoxy group, an alkylthio group, a haloalkylthio group, a cyano group, a nitro group, an optionally substituted phenyl group or an optionally substituted phenoxy group, $R^5$ denotes a hydrogen atom, a fluorine atom or an alkoxy group, or adjacent two of $R^1$ to $R^5$ bind at each end to denote a group represented by CH=CH—CH=CH, a methylenedioxy group optionally substituted by halogen atom(s) or an alkylene group optionally containing one oxygen atom and optionally substituted by an alkyl group, $R^6$ and $R^7$ are the same or different and each denote an optionally substituted hydrocarbon group, and $R^8$ and $R^9$ are the same or different and each denote a hydrogen atom or an alkyl group, or $R^8$ and $R^9$ bind at each end to denote an alkylene group, provided that all of $R^1$ to $R^5$ do not denote hydrogen atoms at the same time, and a pyrazoline derivative represented by the general formula II

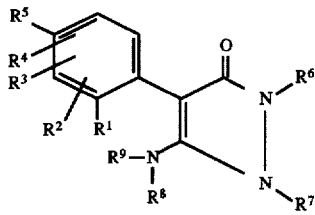

wherein $R^1$ denotes a halogen atom, an alkyl group, a haloalkyl group, an alkoxy group, an alkoxyalkoxy group, a haloalkoxy group, an alkylthio group, a haloalkylthio group, a cyano group, a nitro group, an optionally substituted phenyl group or an optionally substituted phenoxy group, $R^2$ to $R^4$ each denote a hydrogen atom, a halogen atom, an alkyl group, a haloalkyl group, an alkoxy group, a haloalkoxy group, an alkylthio group, a haloalkylthio group, a cyano group, a nitro group, an optionally substituted phenyl group or an optionally substituted phenoxy group, $R^5$ denotes a hydrogen atom, a fluorine atom or an alkoxy group, $R^6$ and $R^7$ are the same or different and each denote an optionally substituted hydrocarbon group, and $R^8$ and $R^9$ are the same or different and each denote a hydrogen atom or an alkyl group, or $R^8$ and $R^9$ bind at each end to denote an alkylene group.

This invention further provides a pyrazoline compound, as a useful intermediate for preparation of the pyrazoline derivatives represented by the above general formula I, represented by the general formula III

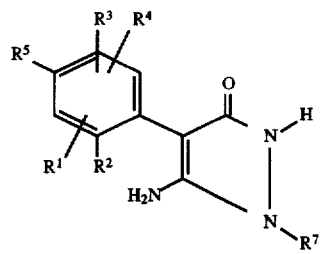

wherein, $R^1$ to $R^4$ each denote a hydrogen atom, a halogen atom, an alkyl group, a haloalkyl group, an alkoxy group, an alkoxyalkoxy group, a haloalkoxy group, an alkylthio group, a haloalkylthio group, a cyano group, a nitro group, an optionally substituted phenyl group or an optionally substituted phenoxy group, $R^5$ denotes a hydrogen atom, a fluorine atom or an alkoxy group, or adjacent two of $R^1$ to $R^5$ bind at each end to denote a group represented by CH=CH—CH=CH, a methylenedioxy group optionally substituted by halogen atom(s) or an alkylene group optionally containing one oxygen atom and optionally substituted by an alkyl group, and $R^7$ denotes an optionally substituted hydrocarbon group having in total 3 to 17 carbon atoms, provided that all of $R^1$ to $R^5$ do not denote hydrogen atoms at the same time.

DETAILED DESCRIPTION OF THE INVENTION

As an embodiment of the pyrazoline compound represented by the general formula III can be mentioned a pyrazoline compound represented by the general formula IV

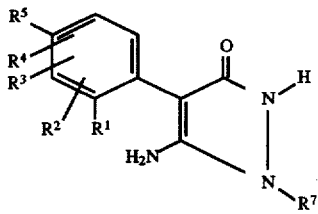

wherein, $R^1$ denotes a halogen atom, an alkyl group, a haloalkyl group, an alkoxy group, an alkoxyalkoxy group, a haloalkoxy group, an alkylthio group, a haloalkylthio group, a cyano group, a nitro group, an optionally substituted phenyl group or an optionally substituted phenoxy group, $R^2$ to $R^4$ each denote a hydrogen atom, a halogen atom, an alkyl group, a haloalkyl group, an alkoxy group, a haloalkoxy group, an alkylthio group, a haloalkylthio group, a cyano group, an optionally substituted phenyl group or an optionally substituted phenoxy group, $R^5$ denotes a hydrogen atom, a fluorine atom or an alkoxy group, and $R^7$ denotes an optionally substituted hydrocarbon group having in total 3 to 17 carbon atoms.

The compounds represented by the general formula I can exist in the state of various tautomerism structures represented by the following formula when $R^8$ and/or $R^9$ are/is hydrogen atom(s), and this invention includes all the possible tautomers.

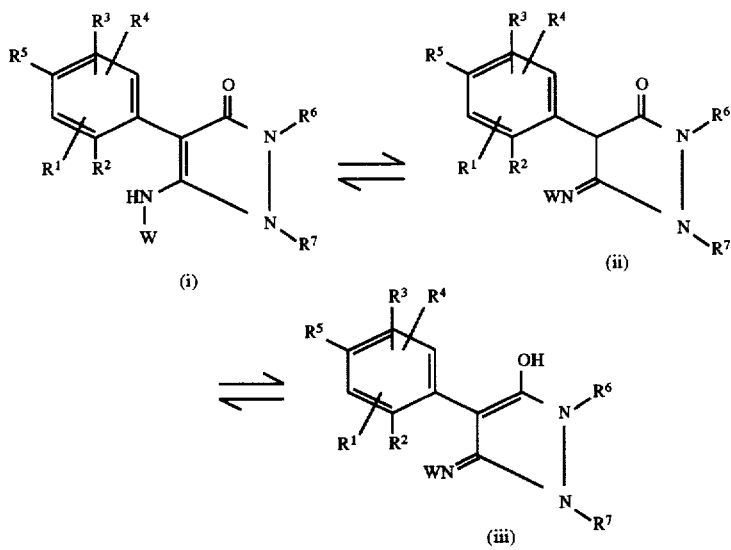

wherein W denotes $R^8$ or $R^9$.

In the substituents $R^1$ to $R^4$ in the pyrazoline derivatives of the general formulae I and II and the pyrazoline compounds of the general formulae III and IV, the halogen atom includes a fluorine atom, a chlorine atom, a bromine atom and an iodine atom, the alkyl group includes a straight-chain or branched chain $C_1$ to $C_5$ alkyl group (e.g., a methyl group, an ethyl group, a n-propyl group, an isopropyl group, a tert-butyl group, etc.), and the haloalkyl group includes a straight-chain or branched chain $C_1$ to $C_5$ alkyl group substituted by the same or different 1 to 11 halogen atoms (e.g., a trifluoromethyl group, a tetrafluoroethyl group, a heptafluoropropyl group, etc.), the alkoxy group includes a straight-chain or branched chain $C_1$ to $C_5$ alkoxy group (e.g., a methoxy group, an ethoxy group, a n-propyloxy group, an isopropyloxy group, etc.), the alkoxyalkoxy group includes a straight-chain or branched chain $(C_1-C_3)$ alkoxy $(C_1-C_3)$ alkoxy group (e.g. $MeOCH_2O$, etc.), the haloalkoxy group includes a straight-chain or branched chain $C_1$ to $C_5$ alkoxy group substituted by the same or different 1 to 11 halogen atoms (e.g., a trifluoromethoxy group, a difluoromethoxy group, a tetrafluoroethoxy group, etc.), the alkylthio group includes a straight-chain or branched chain $C_1$ to $C_5$ alkylthio group (e.g., a methylthio group, an ethylthio group, etc.), the haloalkylthio group includes a straight-chain or branched chain $C_1$ to $C_5$ alkylthio group substituted by the same or different 1 to 11 halogen atoms (e.g., a trifluoromethylthio group, etc.), the optionally substituted phenyl group means a phenyl group optionally substituted by the same or different 1 to 5 substituents, the optionally substituted phenoxy group means a phenoxy group optionally substituted by the same or different 1 to 5 substituents, and the substituents in the optionally substituted phenyl group and the optionally substituted phenoxy group include, for example, halogen atoms (fluorine atoms, chlorine atoms, bromine atoms and, iodine atoms), $C_1$ to $C_5$ alkyl groups (e.g., methyl groups, ethyl groups, etc.), $C_1$ to $C_5$ alkoxy groups (e.g., methoxy groups, ethoxy groups, etc.), $C_1$ to $C_5$ alkylthio groups (e.g., methylthio groups, ethylthio groups, etc.), $C_1$ to $C_5$ haloalkyl groups, preferably $C_1$ to $C_2$ haloalkyl groups (e.g., trifluoromethyl groups, etc.), $C_1$ to $C_5$ haloalkoxy groups, preferably $C_1$ to $C_2$ haloalkoxy groups (e.g., trifluoromethoxy groups, difluoromethoxy groups, etc.), $C_1$ to $C_5$ haloalkylthio groups, preferably $C_1$ to $C_2$ haloalkylthio groups (e.g., trifluoromethylthio groups, etc.), cyano groups, etc., and the alkoxy group for $R^5$ includes a straight-chain or branched chain $C_1$ to $C_5$ alkoxy group (e.g., a methoxy group, an ethoxy group, a n-propyloxy group, an isopropyloxy group).

In the substituents $R_1$ to $R_5$ in the pyrazoline derivatives of the general formula I and the pyrazoline compounds of the general formula III, the methylenedioxy group optionally substituted by halogen atom(s) includes, for example, a methylenedioxy group and a difluoromethylenedioxy group, and the alkylene group (e.g., $C_2$ to $C_6$ alkylene group) optionally containing one oxygen atom and optionally substituted by an alkyl group (e.g., $C_1$ to $C_4$ alkyl group such as a methyl group) includes, for example, a trimethylene group, a tetramethylene group, a group represented by $OCH_2CH_2$, a group represented by $OCH_2CH(CH_3)$, etc.

In the pyrazoline derivatives of the formulae I and II, preferred substituents are a halogen atom (e.g., chlorine, bromine) and an alkyl group (e.g., methyl group) in view of control effect against phytopathogenic fungi.

In the pyrazoline derivatives of the general formulae I and II, preferred substitution positions of $R^1$ to $R^4$ are the 2-position and the 2- and 6-positions in view of control effect against gray molds, and the 3-position and the 2-position in view of control effect against powdery mildews.

The optionally substituted hydrocarbon group for $R^6$ and $R^7$ in the pyrazoline derivatives of the general formulae I and II and for $R^7$ in the pyrazoline compounds of the general formulae III and IV includes a straight-chain or branched chain $C_1$ to $C_{10}$ alkyl group (e.g., an ethyl group, a propyl group, an isopropyl group, a butyl group, an isobutyl group, a sec-butyl group, a 2-methylbutyl group, a 2-ethylpropyl group, a tert-butyl group, etc.), a straight-chain or branched chain $C_2$ to $C_{10}$ alkenyl group (e.g., a 1-methyl-2-propenyl group, etc.), a straight-chain or branched chain $C_2$ to $C_{10}$ alkynyl group (e.g., a 1-methyl-2-propynyl group, etc.), a straight-chain or branched chain $C_1$ to $C_{10}$ alkyl group substituted by the same or different 1 to 21 halogen atoms a straight-chain or branched chain $C_2$ to $C_{10}$ alkenyl group substituted by the same or different 1 to 19 halogen atoms a straight-chain or branched chain $C_2$ to $C_{10}$ alkynyl group substituted by the same or different 1 to 17 halogen atoms a $C_1$ to $C_5$ alkoxy (straight-chain or branched chain) $C_1$ to $C_5$ alkyl group (e.g., a methoxymethyl group, a 1-methoxyethyl group, etc.), a $C_1$ to C5 alkylthio (straight-chain or branched chain) $C_1$ to $C_5$ alkyl group (e.g., a methylthiomethyl group, a 1-methylthioethyl group, etc.), a straight-chain or branched chain $C_1$ to $C_5$ alkyl group substituted by the same or different 1 to 11 halogen atoms, having an $C_1$ to $C_5$ alkoxy group substituted by the same or different 1 to 11 halogen atoms, a straight-chain or branched chain $C_1$ to $C_5$ alkyl group substituted by the same or different 1 to 11 halogen atoms, having an $C_1$ to $C_5$ alkylthio group substituted by the same or different 1 to 11 halogen atoms, a straight-chain or branched chain $C_1$ to $C_5$ alkyl group substituted by a cyano group (e.g., a 1-cyanoethyl group), a straight-chain or branched chain $C_1$ to $C_5$ alkyl group substituted by a $C_1$ to $C_5$ alkoxycarbonyl group (e.g., a 1-(methoxycarbonyl)ethyl group, etc.), a $C_3$ to $C_8$ cycloalkyl group optionally substituted by halogen atom(s) and optionally containing unsaturated bond (s) (e.g., a cyclohexyl group and a cyclopentyl group), a phenyl group optionally substituted by the same or different 1 to 5 substituents [the substituents include, for example, halogen atoms (fluorine atoms, chlorine atoms, bromine atoms and iodine atoms), $C_1$ to $C_5$ alkyl groups (e.g., methyl groups, ethyl groups, etc.), $C_1$ to $C_5$ alkoxy groups (e.g., methoxy groups, ethoxy groups, etc.), $C_1$ to $C_5$ alkylthio groups (e.g., methylthio groups, ethylthio groups, etc.), $C_1$ to $C_5$ haloalkyl groups, preferably $C_1$ to $C_2$ haloalkyl groups (e.g., trifluoromethyl groups, etc.), $C_1$ to $C_5$ haloalkoxy groups, preferably $C_1$ to $C_2$ haloalkoxy groups (e.g., trifluoromethoxy groups, difluoromethoxy groups, etc.), $C_1$ to $C_5$ haloalkylthio groups, preferably $C_1$ to $C_2$ haloalkylthio groups (e.g., trifluoromethylthio groups, etc.), cyano groups, etc.], a $C_7$ to $C_{17}$ aralkyl group (e.g., a benzyl group, an α-methylbenzyl group, an α,α-dimethylbenzyl group, etc.) optionally substituted by the same or different 1 to 5 substituents [the substituents include, for example, halogen atoms (fluorine atoms, chlorine atoms, bromine atoms and iodine atoms), $C_1$ to $C_5$ alkyl groups (e.g., methyl groups, ethyl groups, etc.), $C_1$ to $C_5$ alkoxy groups (e.g., methoxy groups, ethoxy groups, etc.), $C_1$ to $C_5$ alkylthio groups (e.g., methylthio groups, ethylthio groups, etc.), $C_1$ to $C_5$ haloalkyl groups, preferably $C_1$ to $C_2$ haloalkyl groups (e.g., trifluoromethyl groups, etc.), $C_1$ to $C_5$ haloalkoxy groups, preferably $C_1$ to $C_2$ haloalkoxy groups (e.g., trifluoromethoxy groups, difluoromethoxy groups, etc.), $C_1$ to $C_5$ haloalkylthio groups, preferably $C_1$ to $C_2$ haloalkylthio groups (e.g., trifluoromethylthio groups, etc.), cyano groups, etc.].

However, herein, in the compounds of the general formulae III and IV, the optionally substituted hydrocarbon group for $R^7$ includes one having 3 to 17 carbon atoms in total.

In the pyrazoline derivatives of the general formulae I and II, the alkyl group for $R^8$ and $R^9$ includes a $C_1$ to $C_5$ alkyl group (e.g., a methyl group, an ethyl group, a propyl group, an isopropyl group, a butyl group, an isobutyl group, a sec-butyl group, etc.), and the alkylene group formed by bond between $R^8$ and $R^9$ through each end includes a $C_2$ to $C_5$ alkylene group (e.g., a tetramethylene group, a pentamethylene group, an ethylene group, etc.).

In the pyrazoline derivatives of the general formulae I and II, in view of plant disease control effect, one preferred embodiment of $R^6$ and $R^7$ includes a straight-chain or branched chain $C_3$ to $C_{10}$ alkyl group, above all a secondary (the secondary means that there is one branched chain at the a-position of the N atom) $C_3$ to $C_{10}$ alkyl group or a tertiary (the tertiary means that there are two branched chaines at the α-position of the N atom) $C_3$ to $C_{10}$ alkyl group and a secondary or tertiary $C_3$ to $C_{10}$ alkynyl group, and one particularly preferred embodiment of $R^6$ and $R^7$ includes a tert-butyl group, an isopropyl group, a 1-methylbutyl group and a sec-butyl group and 1-ethyl-2-propynyl group, and one preferred embodiment of $R^8$ and $R^9$ includes a hydrogen atom (both $R^8$ and $R^9$) and a $C_1$ to $C_5$ alkyl group (e.g., a methyl group and an ethyl group).

Processes of preparing the pyrazoline derivatives represented by the general formula I are described below.

The pyrazoline derivatives of the general formula I wherein $R^6$ and $R^7$ are optionally substituted tertiary alkyl groups and both $R^8$ and $R^9$ are hydrogen atoms may be prepared by reacting a phenylacetonitrile compound represented by the general formula V

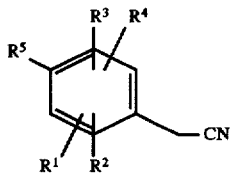

wherein $R^1$ to $R^5$ have the same meanings as in the definitions in the above general formula I, with, usually 1 to 1.5 equivalents thereto of, a diaziridinone derivative represented by the general formula VI

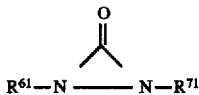

wherein $R^{61}$ and $R^{71}$ are the same or different and each denote an optionally substituted tertiary alkyl group as defined for $R^6$ and $R^7$ of the formula I, usually in a solvent, usually in the presence of 1 to 2 equivalents of a base, usually at −78° to 50° C.

The solvent includes, for example, aromatic hydrocarbons such as benzene, toluene and xylene, ethers such as diethyl ether, diisopropyl ether, dioxane, tetrahydrofuran and ethylene glycol dimethyl ether, nitrites such as actonitrile and isobutyronitrile, acid amides such as N,N-dimethylformamide and N,N-dimethyl-acetamide, sulfur compounds such as dimethyl sulfoxide, and thier mixtures.

The base includes, for example, inorganic bases such as sodium hydride, organic bases such as lithium diisopropylamide, etc.

After the completion of the reaction, the reaction mixture may be neutralized, if necessary, with a dilute acid such as diluted hydrochloric acid, subjected to usual treatments such as organic solvent extraction and/or concentration, and, if necessary, further purified by chromatography, recrystallization, etc. to give the desired compound.

The phenylacetonitrile compounds represented by the general formula V which are raw materials for preparing the pyrazoline derivatives of the general formula I are commercially available, or may be prepared by processes described in Beilstein 9,441, Shin-Jikken Kagaku Koza (New Experimental Chemical Course)(Maruzen Co., Ltd.) 14, [III], 1434 (1985), etc.

The diaziridinone derivatives represented by the general formula VI may be prepared by the process described in The Journal of Organic Chemistry 34, 2254 (1969).

The pyrazoline derivatives of the general formula I wherein $R^8$ and $R^9$ are hydrogen atoms may also be prepared by reacting a pyrazoline compound represented by the general formula III

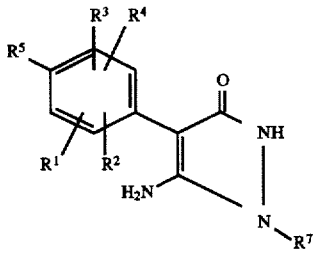

wherein $R^1$ to $R^5$ and $R^7$ have the same meanings as in the definitions in the above general formula I, with, usually 1 to 5 equivalents thereto of, a compound represented by the general formula VIIa, VIIb, VIIc $R^{66}$-X (VIIa), $R^{66}$-$OSO_2Z$ (VIIb), $R^{66}_2$-$SO_4$ (VIIc) wherein $R^{66}$ is an optionally substituted primary or secondary hydrocarbon group (e.g. optionally substituted primary or secondary alkyl, alkenyl or alkynyl group), X denotes a halogen atom (e.g., a chlorine atom, a bromine atom and an iodine atom), and Z denotes a methyl group, a trifluoromethyl group or a phenyl group which may be substituted with a lower alkyl group or a halogen atom. The reaction is usually conducted in a solvent, usually in the presence of 1 to 10 equivalents of an acid binder usually at 30° to 100° C.

The solvent includes, for example, aromatic hydrocarbons such as benzene, toluene and xylene, ethers such as diethyl ether, diisopropyl ether, dioxane, tetrahydrofuran and ethylene glycol dimethyl ether, ketones such as acetone, methyl ethyl ketone, methyl isobutyl ketone, isophorone and cyclohexanone, alcohols such as methanol, ethanol, isopropanol, t-butanol and diethylene glycol, nitriles such as acetonitrile, acid amides such as N,N-dimethylformamide and N,N-dimethyl-acetamide, sulfur compounds such as dimethyl sulfoxide and sulfolane, and thier mixtures.

The acid binder includes, for example, organic bases such as pyridine and triethylamine, inorganic bases such as sodium carbonate, potassium carbonate and sodium hydride, etc.

After the completion of the reaction, the reaction mixture can be subjected to usual post-treatments such as organic solvent extraction and/or concentration, and, if necessary, further purified by chromatography, recrystallization, etc. to give the desired compound.

The pyrazoline derivatives of the general formula I may also be prepared by the process described in Japanese Patent KOKAI (Laid-Open) No. 1-160,968.

The pyrazoline derivatives of the general formula I wherein $R^1$ to $R^9$ are the same as defined above but both $R^8$ and $R^9$ are not hydrogen atoms simultaneously may be prepared by reacting a pyrazoline derivative of the general formula I wherein both $R^8$ and $R^9$ are hydrogen atoms, with, usually 1 to 4 equivalents thereto of, a compound represented by the general formula [X], [XI] or [XII]

$R^{88}$-X  [X]

$R^{88}_2SO_4$  [XI]

wherein $R^{88}$ denotes a primary or secondary alkyl group, or X-$R^{99}$-X [XII] wherein $R^{99}$ denotes an alkylene group and X denotes a chlorine atom, a bromine atom or an iodine atom, usually in a solvent, in the presence of usually 3 to 5 times the amount thereof of a base and usually 0.1 to 1 equivalent of a phase-transfer catalyst, usually at 20° to 120° C.

In this procedure, two identical alkyl groups can be usually introduced to the pyrozoline derivative of the formula I wherein $R^8$ and $R^9$ are hydrogen atoms by using 2 to 4 equivalents of the reagents such as [X] or [XI]. Two different alkyl groups can be usually introduced by reaction steps of using nearly equivalent of the reagent [X] or [XI] in each step in a stepwise manner, and the first step of the reaction steps usually gives monoalkylated pyrazoline derivative.

The solvents which may be used include, for example, aromatic hydrocarbons such as benzene, toluene and xylene, halogenated hydrocarbons such as dichloromethane, chloroform, carbon tetrachloride, dichloroethane and chlorobenzene, ethers such as diethyl ether, diisopropyl ether, dioxane, tetrahydrofuran and ethylene glycol dimethyl ether, ketones such as acetone, methyl ethyl ketone and methyl isobutyl ketone, nitrites such as actonitrile and isobutyronitrile, acid amides such as N,N-dimethylformamide and N,N-dimethylacetamide, water, etc., and thier mixtures.

The base includes, for example, inorganic bases such as sodium hydroxide, potassium hydroxide and potassium carbonate.

The phase-transfer catalyst includes, for example, quaternary ammonium salts such as tetra-n-butylammonium bromide, tetra-n-butylammonium chloride and benzyltriethylammonium chloride, etc.

After the completion of the reaction, the reaction mixture can be subjected to usual post-treatments such as organic solvent extraction and/or concentration, and, if necessary, further purified by chromatography, recrystallization, etc. to give the desired compound.

Specific examples of the pyrazoline derivatives of the general formula I are shown below in the following chemical formulae.

Therein, "Me" means methyl, "Et" means ethyl, "nPr or Pr" means n-propyl, "Ph" means phenyl and "$HC_2F_4$" means $HCF_2CF_2$.

Compounds represented by the general formulae

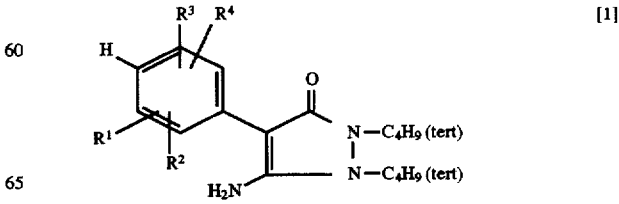

[1]

-continued

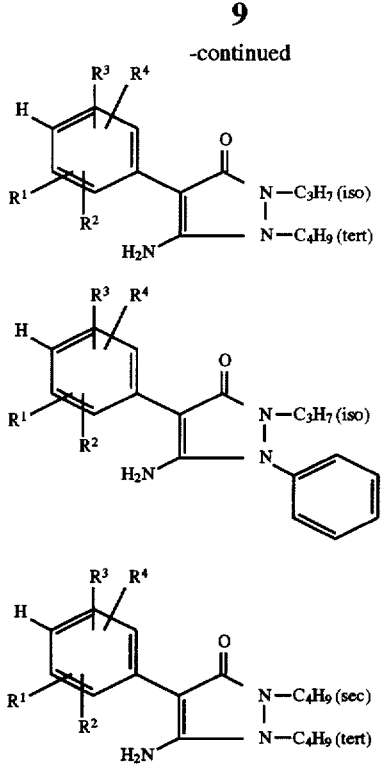

and

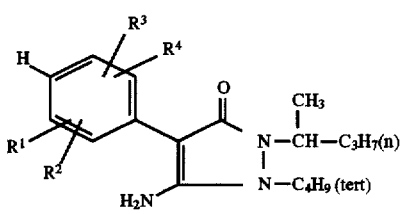

wherein, the substituents of $R^1$ to $R^4$ denote those shown in Table 1 to Table 15.

TABLE 1

| $R^1 \sim R^4$ | $R^1 \sim R^4$ |
| --- | --- |
| 2-F | 3-iPrO |
| 3-F | 2-CF$_3$ |
| 2-Cl | 3-CF$_3$ |
| 3-Cl | 2-C$_2$F$_5$ |
| 2-Br | 3-C$_2$F$_5$ |
| 3-Br | 2-C$_3$F$_7$ |
| 2-I | 3-C$_3$F$_7$ |
| 3-I | 2-CF$_3$O |
| 2-CH$_3$ | 3-CF$_3$O |
| 3-CH$_3$ | 2-CF$_2$HO |
| 2-Et | 3-CF$_2$HO |
| 3-Et | 2-C$_2$F$_5$O |
| 2-nPr | 3-C$_2$F$_5$O |
| 3-nPr | 2-CF$_2$ClO |
| 2-iPr | 3-CF$_2$ClO |
| 3-iPr | 2-CF$_2$BrO |
| 2-MeO | 3-CF$_2$BrO |
| 3-MeO | 2-HCF$_2$CF$_2$O |
| 2-EtO | 3-HCF$_2$CF$_2$O |
| 3-EtO | 2-PhO |
| 2-nPrO | 3-PhO |
| 3-nPrO | 2-MeOCH$_2$O |
| 2-iPrO | 3-MeOCH$_2$O |

TABLE 2

| $R^1 \sim R^4$ | $R^1 \sim R^4$ |
| --- | --- |
| 2-CN | 2-F, 5-CH$_3$ |
| 3-CN | 2-F, 6-CH$_3$ |
| 2-CH$_3$S | 2-F, 3-C$_2$H$_5$ |
| 3-CH$_3$S | 2-F, 5-C$_2$H$_5$ |
| 2-EtS | 2-F, 6-C$_2$H$_5$ |
| 3-EtS | 2-F, 3-MeO |
| 2-CF$_3$S | 2-F, 5-MeO |
| 3-CF$_3$S | 2-F, 6-MeO |
| 2-CF$_2$HS | 2-F, 3-EtO |
| 3-CF$_2$HS | 2-F, 5-EtO |
| 2-HC$_2$F$_4$S | 2-F, 6-EtO |
| 3-HC$_2$F$_4$S | 2-F, 3-CF$_3$ |
| 2-PhO | 2-F, 5-CF$_3$ |
| 3-PhO | 2-F, 6-CF$_3$ |
| 2,3-F$_2$ | 2-F, 3-CF$_3$O |
| 2,5-F$_2$ | 2-F, 5-CF$_3$O |
| 2,6-F$_2$ | 2-F, 6-CF$_3$O |
| 2-F, 3-Cl | 2-F, 3-CF$_2$HO |
| 2-F, 5-Cl | 2-F, 5-CF$_2$HO |
| 2-F, 6-Cl | 2-F, 6-CF$_2$HO |
| 2-F, 3-Br | 2-F, 3-CH$_3$S |
| 2-F, 5-Br | 2-F, 5-CH$_3$S |
| 2-F, 6-Br | 2-F, 6-CH$_3$S |
| 2-F, 3-CH$_3$ | 2-F, 3-CF$_3$S |

TABLE 3

| $R^1 \sim R^4$ | $R^1 \sim R^4$ |
| --- | --- |
| 2-F, 5-CF$_3$S | 2-Cl, 5-MeO |
| 2-F, 6-CF$_3$S | 2-Cl, 6-MeO |
| 2-F, 3-CN | 2-Cl, 3-EtO |
| 2-F, 5-CN | 2-Cl, 5-EtO |
| 2-F, 6-CN | 2-Cl, 6-EtO |
| 2-F, 3-HC$_2$F$_4$O | 2-Cl, 3-CF$_3$ |
| 2-F, 5-HC$_2$F$_4$O | 2-Cl, 5-CF$_3$ |
| 2-F, 6-HC$_2$F$_4$O | 2-Cl, 6-CF$_3$ |
| 2-Cl, 3-F | 2-Cl, 3-CF$_3$O |
| 2-Cl, 5-F | 2-Cl, 5-CF$_3$O |
| 2,3-Cl$_2$ | 2-Cl, 6-CF$_3$O |
| 2,5-Cl$_2$ | 2-Cl, 3-CF$_2$HO |
| 2,6-Cl$_2$ | 2-Cl, 5-CF$_2$HO |
| 2-Cl, 3-Br | 2-Cl, 6-CF$_2$HO |
| 2-Cl, 5-Br | 2-Cl, 3-CH$_3$S |
| 2-Cl, 6-Br | 2-Cl, 5-CH$_3$S |
| 2-Cl, 3-CH$_3$ | 2-Cl, 6-CH$_3$S |
| 2-Cl, 5-CH$_3$ | 2-Cl, 3-CF$_3$S |
| 2-Cl, 6-CH$_3$ | 2-Cl, 5-CF$_3$S |
| 2-Cl, 3-Et | 2-Cl, 6-CF$_3$S |
| 2-Cl, 5-Et | 2-Cl, 3-CN |
| 2-Cl, 6 Et | 2-Cl, 5-CN |
| 2-Cl, 3-MeO | 2-Cl, 6-CN |

TABLE 4

| $R^1 \sim R^4$ | $R^1 \sim R^4$ |
| --- | --- |
| 2-Cl, 3-HC$_2$F$_4$O | 2-Br, 3-CF$_3$ |
| 2-Cl, 5-HC$_2$F$_4$O | 2-Br, 5-CF$_3$ |
| 2-Cl, 6-HC$_2$F$_4$O | 2-Br, 6-CF$_3$ |
| 2-Br, 3-F | 2-Br, 3-CF$_3$O |
| 2-Br, 5-F | 2-Br, 5-CF$_3$O |
| 2-Br, 3-Cl | 2-Br, 6-CF$_3$O |
| 2-Br, 5-Cl | 2-Br, 3-CF$_2$HO |
| 2,3-Br$_2$ | 2-Br, 5-CF$_2$HO |
| 2,5-Br$_2$ | 2-Br, 6-CF$_2$HO |
| 2,6-Br$_2$ | 2-Br, 3-CH$_3$S |
| 2-Br, 3-Me | 2-Br, 5-CH$_3$S |
| 2-Br, 5-Me | 2-Br, 6-CH$_3$S |
| 2-Br, 6-Me | 2-Br, 3-CF$_3$S |
| 2-Br, 3-Et | 2-Br, 5-CF$_3$S |
| 2-Br, 5-Et | 2-Br, 6-CF$_3$S |

TABLE 4-continued

| $R^1$–$R^4$ | $R^1$–$R^4$ |
| --- | --- |
| 2-Br, 6-Et | 2-Br, 3-CN |
| 2-Br, 3-MeO | 2-Br, 5-CN |
| 2-Br, 5-MeO | 2-Br, 6-CN |
| 2-Br, 6-MeO | 2-Br, 3-HC$_2$F$_4$O |
| 2-Br, 3-EtO | 2-Br, 5-HC$_2$F$_4$O |
| 2-Br, 5-EtO | 2-Br, 6-HC$_2$F$_4$O |
| 2-Br, 6-EtO | 2-I, 3F |

TABLE 5

| $R^1$–$R^4$ | $R^1$–$R^4$ |
| --- | --- |
| 2-I, 5-F | 2-CH$_3$, 6-CF$_3$O |
| 2-CH$_3$, 3-F | 2-CH$_3$, 3-CF$_2$HO |
| 2-CH$_3$, 5-F | 2-CH$_3$, 5-CF$_2$HO |
| 2-CH$_3$, 3-Cl | 2-CH$_3$, 6-CF$_2$HO |
| 2-CH$_3$, 5-Cl | 2-CH$_3$, 3-CH$_3$S |
| 2-CH$_3$, 3-Br | 2-CH$_3$, 5-CH$_3$S |
| 2-CH$_3$, 5-Br | 2-CH$_3$, 6-CH$_3$S |
| 2,3-(CH$_3$)$_2$ | 2-CH$_3$, 3-CF$_3$S |
| 2,5-(CH$_3$)$_2$ | 2-CH$_3$, 5-CF$_3$S |
| 2,6-(CH$_3$)$_2$ | 2-CH$_3$, 6-CF$_3$S |
| 2-CH$_3$, 3-Et | 2-CH$_3$, 3-CN |
| 2-CH$_3$, 5-Et | 2-CH$_3$, 5-CN |
| 2-CH$_3$, 6-Et | 2-CH$_3$, 6-CN |
| 2-CH$_3$, 3-MeO | 2-CH$_3$, 3-HC$_2$F$_4$O |
| 2-CH$_3$, 5-MeO | 2-CH$_3$, 5-HC$_2$F$_4$O |
| 2-CH$_3$, 6-MeO | 2-CH$_3$, 6-HC$_2$F$_4$O |
| 2-CH$_3$, 3-EtO | 2-Et, 3-F |
| 2-CH$_3$, 5-EtO | 2-Et, 5-F |
| 2-CH$_3$, 6-EtO | 2-Et, 3-Cl |
| 2-CH$_3$, 3-CF$_3$ | 2-Et, 5-Cl |
| 2-CH$_3$, 5-CF$_3$ | 2-Et, 3-Br |
| 2-CH$_3$, 6-CF$_3$ | 2-Et, 5-Br |
| 2-CH$_3$, 3-CF$_3$O | 2-Et, 3-CH$_3$ |
| 2-CH$_3$, 5-CF$_3$O | 2-Et, 5-CH$_3$ |

TABLE 6

| $R^1$–$R^4$ | $R^1$–$R^4$ |
| --- | --- |
| 2,3-Et$_2$ | 2-Et, 6-CF$_3$S |
| 2,5-Et$_2$ | 2-Et, 3-CN |
| 2,6-Et$_2$ | 2-Et, 5-CN |
| 2-Et, 3-MeO | 2-Et, 6-CN |
| 2-Et, 5-MeO | 2-Et, 3-HC$_2$F$_4$O |
| 2-Et, 6-MeO | 2-Et, 5-HC$_2$F$_4$O |
| 2-Et, 3-EtO | 2-Et, 6-HC$_2$F$_4$O |
| 2-Et, 5-EtO | 2-MeO, 3-F |
| 2-Et, 6-EtO | 2-MeO, 5-F |
| 2-Et, 3-CF$_3$ | 2-MeO, 3-Cl |
| 2-Et, 5-CF$_3$ | 2-MeO, 5-Cl |
| 2-Et, 6-CF$_3$ | 2-MeO, 3-Br |
| 2-Et, 3-CF$_3$O | 2-MeO, 5-Br |
| 2-Et, 5-CF$_3$O | 2-MeO, 3-CH$_3$ |
| 2-Et, 6-CF$_3$O | 2-MeO, 5-CH$_3$ |
| 2-Et, 3-CF$_2$HO | 2-MeO, 3-Et |
| 2-Et, 5-CF$_2$HO | 2-MeO, 5-Et |
| 2-Et, 6-CF$_2$HO | 2,3-(MeO)$_2$ |
| 2-Et, 3-CH$_3$S | 2,5-(MeO)$_2$ |
| 2-Et, 5-CH$_3$S | 2,6-(MeO)$_2$ |
| 2-Et, 6-CH$_3$S | 2-MeO, 3-EtO |
| 2-Et, 3-CF$_3$S | 2-MeO, 5-EtO |
| 2-Et, 5-CF$_3$S | 2-MeO, 6-EtO |

TABLE 7

| $R^1$–$R^4$ | $R^1$–$R^4$ |
| --- | --- |
| 2-MeO, 3-CF$_3$ | 2-EtO, 3-Cl |
| 2-MeO, 5-CF$_3$ | 2-EtO, 5-Cl |
| 2-MeO, 6-CF$_3$ | 2-EtO, 3-Br |
| 2-MeO, 3-CF$_3$O | 2-EtO, 5-Br |
| 2-MeO, 5-CF$_3$O | 2-EtO, 3-CH$_3$ |
| 2-MeO, 6-CF$_3$O | 2-EtO, 5-CH$_3$ |
| 2-MeO, 3-CF$_2$HO | 2-EtO, 3-Et |
| 2-MeO, 5-CF$_2$HO | 2-EtO, 5-Et |
| 2-MeO, 6-CF$_2$HO | 2-EtO, 3-MeO |
| 2-MeO, 3-CH$_3$S | 2-EtO, 5-MeO |
| 2-MeO, 5-CH$_3$S | 2,3-(EtO)$_2$ |
| 2-MeO, 6-CH$_3$S | 2,5-(EtO)$_2$ |
| 2-MeO, 3-CF$_3$S | 2,6-(EtO)$_2$ |
| 2-MeO, 5-CF$_3$S | 2-EtO, 3-CF$_3$ |
| 2-MeO, 6-CF$_3$S | 2-EtO, 5-CF$_3$ |
| 2-MeO, 3-CN | 2-EtO, 6-CF$_3$ |
| 2-MeO, 5-CN | 2-EtO, 3-CF$_3$O |
| 2-MeO, 6-CN | 2-EtO, 5-CF$_3$O |
| 2-MeO, 3-HC$_2$F$_4$O | 2-EtO, 6-CF$_3$O |
| 2-MeO, 5-HC$_2$F$_4$O | 2-EtO, 3-CF$_2$HO |
| 2-MeO, 6-HC$_2$F$_4$O | 2-EtO, 5-CF$_2$HO |
| 2-EtO, 3-F | 2-EtO, 6-CF$_2$HO |
| 2-EtO, 5-F | 2-EtO, 3-CH$_3$S |

TABLE 8

| $R^1$–$R^4$ | $R^1$–$R^4$ |
| --- | --- |
| 2-EtO, 5-CH$_3$S | 2-CF$_3$, 5-MeO |
| 2-EtO, 6-CH$_3$S | 2-CF$_3$, 3-EtO |
| 2-EtO, 3-CF$_3$S | 2-CF$_3$, 5-EtO |
| 2-EtO, 5-CF$_3$S | 2-CF$_3$, 3-CF$_3$ |
| 2-EtO, 6-CF$_3$S | 2-CF$_3$, 5-CF$_3$ |
| 2-EtO, 3-CN | 2-CF$_3$, 6-CF$_3$ |
| 2-EtO, 5-CN | 2-CF$_3$, 3-CF$_3$O |
| 2-EtO, 6-CN | 2-CF$_3$, 5-CF$_3$O |
| 2-EtO, 3-HC$_2$F$_4$O | 2-CF$_3$, 6-CF$_3$O |
| 2-EtO, 5-HC$_2$F$_4$O | 2-CF$_3$, 3-CF$_2$HO |
| 2-EtO, 6-HC$_2$F$_4$O | 2-CF$_3$, 5-CF$_2$HO |
| 2-CF$_3$, 3-F | 2-CF$_3$, 6-CF$_2$HO |
| 2-CF$_3$, 5-F | 2-CF$_3$, 3-CH$_3$S |
| 2-CF$_3$, 3-Cl | 2-CF$_3$, 5-CH$_3$S |
| 2-CF$_3$, 5-Cl | 2-CF$_3$, 6-CH$_3$S |
| 2-CF$_3$, 3-Br | 2-CF$_3$, 3-CF$_3$S |
| 2-CF$_3$, 5-Br | 2-CF$_3$, 5-CF$_3$S |
| 2-CF$_3$, 3-CH$_3$ | 2-CF$_3$, 6-CF$_3$S |
| 2-CF$_3$, 5-CH$_3$ | 2-CF$_3$, 3-CN |
| 2-CF$_3$, 3-Et | 2-CF$_3$, 5-CN |
| 2-CF$_3$, 5-Et | 2-CF$_3$, 6-CN |
| 2-CF$_3$, 3-MeO | 2-CF$_3$, 3-HC$_2$F$_4$O |

TABLE 9

| $R^1$–$R^4$ | $R^1$–$R^4$ |
| --- | --- |
| 2-CF$_3$, 5-HC$_2$F$_4$O | 2-CF$_3$O, 6-CF$_2$HO |
| 2-CF$_3$, 6-HC$_2$F$_4$O | 2-CF$_3$O, 3-CH$_3$S |
| 2-CF$_3$O, 3-F | 2-CF$_3$O, 5-CH$_3$S |
| 2-CF$_3$O, 5-F | 2-CF$_3$O, 6-CH$_3$S |
| 2-CF$_3$O, 3-Cl | 2-CF$_3$O, 3-CF$_3$S |
| 2-CF$_3$O, 5-Cl | 2-CF$_3$O, 5-CF$_3$S |
| 2-CF$_3$O, 3-Br | 2-CF$_3$O, 6-CF$_3$S |
| 2-CF$_3$O, 5-Br | 2-CF$_3$O, 3-CN |
| 2-CF$_3$O, 3-CH$_3$ | 2-CF$_3$O, 5-CN |
| 2-CF$_3$O, 5-CH$_3$ | 2-CF$_3$O, 6-CN |
| 2-CF$_3$O, 3-Et | 2-CF$_3$O, 3-HC$_2$F$_4$O |
| 2-CF$_3$O, 5-Et | 2-CF$_3$O, 5-HC$_2$F$_4$O |
| 2-CF$_3$O, 3-MeO | 2-CF$_3$O, 6-HC$_2$F$_4$O |
| 2-CF$_3$O, 5-MeO | 2-CF$_2$HO, 3-F |
| 2-CF$_3$O, 3-EtO | 2-CF$_2$HO, 5-F |
| 2-CF$_3$O, 5-EtO | 2-CF$_2$HO, 3-Cl |
| 2-CF$_3$O, 3-CF$_3$ | 2-CF$_2$HO, 5-Cl |

TABLE 9-continued

| R¹~R⁴ | R¹~R⁴ |
|---|---|
| 2-CF₃O, 5-CF₃ | 2-CF₂HO, 3-Br |
| 2-CF₃O, 3-CF₃O | 2-CF₂HO, 5-Br |
| 2-CF₃O, 5-CF₃O | 2-CF₂HO, 3-Me |
| 2-CF₃O, 6-CF₃O | 2-CF₂HO, 5-Me |
| 2-CF₃O, 3-CF₂HO | 2-CF₂HO, 3-Et |
| 2-CF₃O, 5-CF₂HO | 2-CF₂HO, 5-Et |

TABLE 10

| R¹~R⁴ | R¹~R⁴ |
|---|---|
| 2-CF₂HO, 3-MeO | 2-CH₃S, 5-Cl |
| 2-CF₂HO, 5-MeO | 2-CH₃S, 3-Br |
| 2-CF₂HO, 3-EtO | 2-CH₃S, 5-Br |
| 2-CF₂HO, 5-EtO | 2-CH₃S, 3-CH₃ |
| 2-CF₂HO, 3-CF₃ | 2-CH₃S, 5-CH₃ |
| 2-CF₂HO, 5-CF₃ | 2-CH₃S, 3-Et |
| 2-CF₂HO, 3-CF₂HO | 2-CH₃S, 5-Et |
| 2-CF₂HO, 5-CF₂HO | 2-CH₃S, 3-MeO |
| 2-CF₂HO, 6-CF₂HO | 2-CH₃S, 5-MeO |
| 2-CF₂HO, 3-CH₃S | 2-CH₃S, 3-EtO |
| 2-CF₂HO, 5-CH₃S | 2-CH₃S, 5-EtO |
| 2-CF₂HO, 6-CH₃S | 2-CH₃S, 3-CF₃ |
| 2-CF₂HO, 3-CF₃S | 2-CH₃S, 5-CF₃ |
| 2-CF₂HO, 5-CF₃S | 2-CH₃S, 3-CF₃O |
| 2-CF₂HO, 6-CF₃S | 2-CH₃S, 5-CF₃O |
| 2-CF₂HO, 3-CN | 2-CH₃S, 3-CF₂HO |
| 2-CF₂HO, 5-CN | 2-CH₃S, 5-CF₂HO |
| 2-CF₂HO, 6-CN | 2-CH₃S, 3-CH₃S |
| 2-CF₂HO, 3-HC₂F₄O | 2-CH₃S, 5-CH₃S |
| 2-CF₂HO, 5-HC₂F₄O | 2-CH₃S, 6-CH₃S |
| 2-CF₂HO, 6-HC₂F₄O | 2-CH₃S, 3-CF₃S |
| 2-CH₃S, 3-F | 2-CH₃S, 5-CF₃S |
| 2-CH₃S, 5-F | 2-CH₃S, 6-CF₃S |
| 2-CH₃S, 3-Cl | 2-CH₃S, 3-CN |

TABLE 11

| R¹~R⁴ | R¹~R⁴ |
|---|---|
| 2-CH₃S, 5-CN | 2-CF₃S, 3-CF₂HO |
| 2-CH₃S, 6-CN | 2-CF₃S, 5-CF₂HO |
| 2-CH₃S, 3-HC₂F₄O | 2-CF₃S, 3-CH₃S |
| 2-CH₃S, 5-HC₂F₄O | 2-CF₃S, 5-CH₃S |
| 2-CH₃S, 6-HC₂F₄O | 2-CF₃S, 3-CF₃S |
| 2-CF₃S, 3-F | 2-CF₃S, 5-CF₃S |
| 2-CF₃S, 5-F | 2-CF₃S, 6-CF₃S |
| 2-CF₃S, 3-Cl | 2-CF₃S, 3-CN |
| 2-CF₃S, 5-Cl | 2-CF₃S, 5-CN |
| 2-CF₃S, 3-Br | 2-CF₃S, 6-CN |
| 2-CF₃S, 5-Br | 2-CF₃S, 3-HC₂F₄O |
| 2-CF₃S, 3-Me | 2-CF₃S, 5-HC₂F₄O |
| 2-CF₃S, 5-Me | 2-CF₃S, 6-HC₂F₄O |
| 2-CF₃S, 3-Et | 2-CN, 3-F |
| 2-CF₃S, 5-Et | 2-CN, 5-F |
| 2-CF₃S, 3-MeO | 2-CN, 3-Cl |
| 2-CF₃S, 5-MeO | 2-CN, 5-Cl |
| 2-CF₃S, 3-EtO | 2-CN, 3-Br |
| 2-CF₃S, 5-EtO | 2-CN, 5-Br |
| 2-CF₃S, 3-CF₃ | 2-CN, 3-Et |
| 2-CF₃S, 5-CF₃ | 2-CN, 5-Et |
| 2-CF₃S, 3-CF₃O | 2-CN, 3-CH₃ |
| 2-CF₃S, 5-CF₃O | 2-CN, 5-CH₃ |

TABLE 12

| R¹~R⁴ | R¹~R⁴ |
|---|---|
| 2-CN, 3-MeO | 2-HC₂F₄O, 3-Cl |
| 2-CN, 5-MeO | 2-HC₂F₄O, 5-Cl |

TABLE 12-continued

| R¹~R⁴ | R¹~R⁴ |
|---|---|
| 2-CN, 3-EtO | 2-HC₂F₄O, 3-Br |
| 2-CN, 5-EtO | 2-HC₂F₄O, 5-Br |
| 2-CN, 3-CF₃ | 2-HC₂F₄O, 3-Me |
| 2-CN, 5-CF₃ | 2-HC₂F₄O, 5-Me |
| 2-CN, 3-CF₃O | 2-HC₂F₄O, 3-Et |
| 2-CN, 5-CF₃O | 2-HC₂F₄O, 5-Et |
| 2-CN, 3-CF₂HO | 2-HC₂F₄O, 3-MeO |
| 2-CN, 5-CF₂HO | 2-HC₂F₄O, 5-MeO |
| 2-CN, 3-CH₃S | 2-HC₂F₄O, 3-EtO |
| 2-CN, 5-CH₃S | 2-HC₂F₄O, 5-EtO |
| 2-CN, 3-CF₃S | 2-HC₂F₄O, 3-CF₃ |
| 2-CN, 5-CF₃S | 2-HC₂F₄O, 5-CF₃ |
| 2-CN, 3-CN | 2-HC₂F₄O, 3-CF₃O |
| 2-CN, 5-CN | 2-HC₂F₄O, 5-CF₃O |
| 2-CN, 6-CN | 2-HC₂F₄O, 3-CF₂HO |
| 2-CN, 3-HC₂F₄O | 2-HC₂F₄O, 5-CF₂HO |
| 2-CN, 5-HC₂F₄O | 2-HC₂F₄O, 3-CH₃S |
| 2-CN, 6-HC₂F₄O | 2-HC₂F₄O, 5-CH₃S |
| 2-HC₂F₄O, 3-F | 2-HC₂F₄O, 3-CF₃S |
| 2-HC₂F₄O, 5-F | 2-HC₂F₄O, 5-CF₃S |

TABLE 13

| R¹~R⁴ | R¹~R⁴ |
|---|---|
| 2-HC₂F₄O, 3-CN | 3-Cl, 5-CH₃ |
| 2-HC₂F₄O, 5-CN | 3-Cl, 5-Et |
| 2,3-(HC₂F₄O)₂ | 3-Cl, 5-MeO |
| 2,5-(HC₂F₄O)₂ | 3-Cl, 5-EtO |
| 2,6-(HC₂F₄O)₂ | 3-Cl, 5-CF₃ |
| 3,5-F₂ | 3-Cl, 5-CF₃O |
| 3-F, 5-Cl | 3-Cl, 5-CF₂HO |
| 3-F, 5-Br | 3-Cl, 5-CH₃S |
| 3-F, 5-I | 3-Cl, 5-CF₃S |
| 3-F, 5-CH₃ | 3-Cl, 5-CN |
| 3-F, 5-Et | 3-Cl, 5-HC₂F₄O |
| 3-F, 5-MeO | 3,5-Br₂ |
| 3-F, 5-EtO | 3-Br, 5-I |
| 3-F, 5-CF₃ | 3-Br, 5-CH₃ |
| 3-F, 5-CF₃O | 3-Br, 5-Et |
| 3-F, 5-CF₂HO | 3-Br, 5-MeO |
| 3-F, 5-CH₃S | 3-Br, 5-EtO |
| 3-F, 5-CF₃S | 3-Br, 5-CF₃ |
| 3-F, 5-CN | 3-Br, 5-CF₃O |
| 3-F, 5-HC₂F₄O | 3-Br, 5-CF₂HO |
| 3,5-Cl₂ | 3-Br, 5-CH₃S |
| 3-Cl, 5-Br | 3-Br, 5-CF₃S |
| 3-Cl, 5-I | 3-Br, 5-CN |

TABLE 14

| R¹~R⁴ | R¹~R⁴ |
|---|---|
| 3-Br, 5-HC₂F₄O | 3-MeO, 5-EtO |
| 3,5-(CH₃)₂ | 3-MeO, 5-CF₃ |
| 3-CH₃, 5-Et | 3-MeO, 5-CF₃O |
| 3-CH₃, 5-MeO | 3-MeO, 5-CF₂HO |
| 3-CH₃, 5-EtO | 3-MeO, 5-CH₃S |
| 3-CH₃, 5-CF₃ | 3-MeO, 5-CF₃S |
| 3-CH₃, 5-CF₃O | 3-MeO, 5-CN |
| 3-CH₃, 5-CF₂HO | 3-MeO, 5-HC₂F₄O |
| 3-CH₃, 5-CH₃S | 3,5-(EtO)₂ |
| 3-CH₃, 5-CF₃S | 3-EtO, 5-CF₃ |
| 3-CH₃, 5-CN | 3-EtO, 5-CF₃O |
| 3-CH₃, 5-HC₂F₄O | 3-EtO, 5-CF₂HO |
| 3,5-(Et)₂ | 3-EtO, 5-CH₃S |
| 3-Et, 5-MeO | 3-EtO, 5-CF₃S |
| 3-Et, 5-EtO | 3-EtO, 5-CN |
| 3-Et, 5-CF₃ | 3-EtO, 5-HC₂F₄O |
| 3-Et, 5-CF₃O | 3,5-(CF₃)₂ |
| 3-Et, 5-CF₂HO | 3-CF₃, 5-CF₃O |
| 3-Et, 5-CH₃S | 3-CF₃, 5-CF₂HO |

TABLE 14-continued

| R¹~R⁴ | R¹~R⁴ |
|---|---|
| 3-Et, 5-CF₃S | 3-CF₃, 5-CH₃S |
| 3-Et, 5-CN | 3-CF₃, 5-CF₃S |
| 3-Et, 5-HC₂F₄O | 3-CF₃, 5-CN |
| 3,5-(MeO)₂ | 3-CF₃, 5-HC₂F₄O |

TABLE 15

| R¹~R⁴ | R¹~R⁴ |
|---|---|
| 3,5-(CF₃O)₂ | 3-CF₃S, 5-HC₂F₄O |
| 3-CF₃O, 5-CF₂HO | 3,5-(CN)₂ |
| 3-CF₃O, 5-CH₃S | 3-CN, 5-HC₂F₄O |
| 3-CF₃O, 5-CF₃S | 3,5-(HC₂F₄O)₂ |
| 3-CF₃O, 5-CN | 2,3,5-F₃ |
| 3-CF₃O, 5-HC₂F₄O | 2,3,6-F₃ |
| 3,5-(CF₂HO)₂ | 2,3,5-Cl₃ |
| 3-CF₂HO, 5-CH₃S | 2,3,6-Cl₃ |
| 3-CF₂HO, 5-CF₃S | 2,3,5-(CH₃)₃ |
| 3-CF₂HO, 5-CN | 2,3,6-(CH₃)₃ |
| 3-CF₂HO, 5-HC₂F₄O | 2,3,5-(CH₃O)₃ |
| 3,5-(CH₃S)₂ | 2,3,6-(CH₃O)₃ |
| 3-CH₃S, 5-CF₃S | 2,3,5-Br₃ |
| 3-CH₃S, 5-CN | 2,3,6-Br₃ |
| 3-CH₃S, 5-HC₂F₄O | 2,3,5,6-F₄ |
| 3,5-(CF₃S)₂ | 2,3,5,6-Cl₄ |
| 3-CF₃S, 5-CN | |

Compounds represented by the general formulae

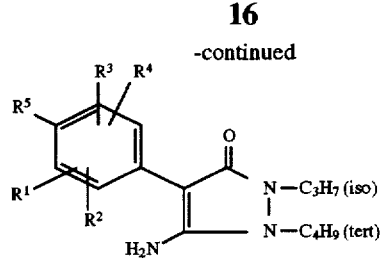

[6]

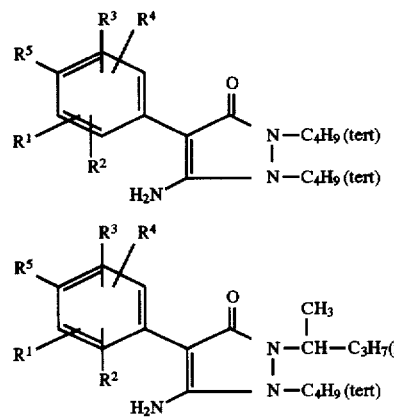

[7]

[8]

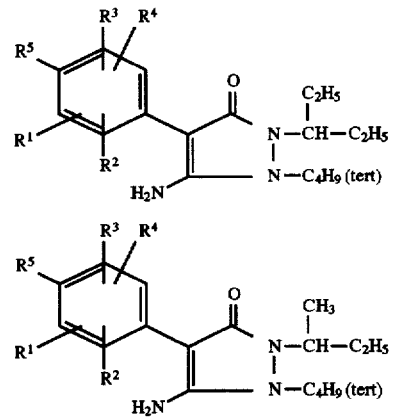

[9]

and

[10]

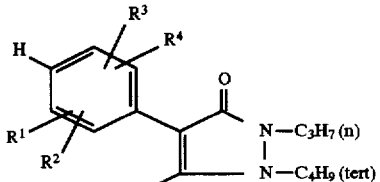

wherein, the substituents of R¹ to R⁴ denote those shown in Table 16 and Table 17, and R⁵ denotes a fluorine atom, a methoxy group or an ethoxy group.

TABLE 16

| R¹~R⁴ | R¹~R⁴ |
|---|---|
| H | 3-CF₃ |
| 2-F | 3-CF₃O |
| 2-Cl | 3-CF₂HO |
| 2-Br | 3-CH₃S |
| 2-I | 3-CF₃S |
| 2-CH₃ | 3-CN |
| 2-Et | 3-HC₂F₄O |
| 2-MeO | 2,3-F₂ |
| 2-CF₃ | 2,5-F₂ |
| 2-CF₃O | 2,6-F₂ |
| 2-CF₂HO | 2,3-Cl₂ |
| 2-CH₃S | 2,5-Cl₂ |
| 2-CF₃S | 2,6-Cl₂ |
| 2-CN | 2,3-(CH₃)₂ |
| 2-HC₂F₄O | 2,5-(CH₃)₂ |
| 3-F | 2,6-(CH₃)₂ |
| 3-Cl | 2,3-(CH₃O)₂ |
| 3-Br | 2,5-(CH₃O)₂ |
| 3-CH₃ | 2,6-(CH₃O)₂ |
| 3-Et | 2,3-Br₂ |
| 3-MeO | 2,5-Br₂ |
| 3-EtO | 2,6-Br₂ |

TABLE 17

| R¹~R⁴ | R¹~R⁴ |
|---|---|
| 3,5-F₂ | 2,3,5,6-F₄ |
| 3,5-Cl₂ | 2,3,5,6-Cl₄ |
| 3,5-Br₂ | 2,3-F₂, 6-Cl |
| 3,5-(CH₃)₂ | 2,5-F₂, 6-Cl |
| 3,5-(CH₃O)₂ | |

Compounds represented by the general formulae

[11]

[12]

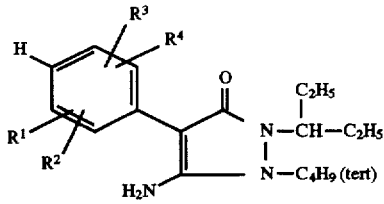

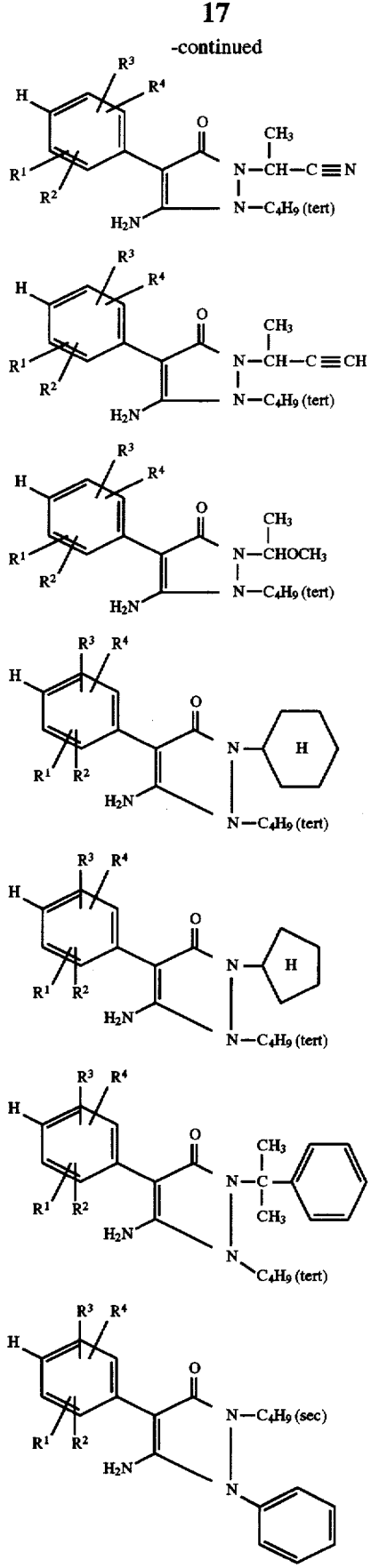

-continued

[13]

[14]

[15]

[16]

[17]

[18]

[19]

[20]

[21]

wherein, the substituents of $R^1$ to $R^4$ denote those shown in Table 18 and Table 19.

TABLE 18

| $R^1$–$R^4$ | $R^1$–$R^4$ |
|---|---|
| 2-F | 3-iPrO |
| 3-F | 2-$CF_3$ |
| 2-Cl | 3-$CF_3$ |
| 3-Cl | 2-$C_2F_5$ |
| 2-Br | 3-$C_2F_5$ |
| 3-Br | 2-$C_3F_7$ |
| 2-I | 3-$C_3F_7$ |
| 3-I | 2-$CF_3O$ |
| 2-$CH_3$ | 3-$CF_3O$ |
| 3-$CH_3$ | 2-$CF_2HO$ |
| 2-Et | 3-$CF_2HO$ |
| 3-Et | 2-$C_2F_5O$ |
| 2-nPr | 3-$C_2F_5O$ |
| 3-nPr | 2-$CF_2ClO$ |
| 2-iPr | 3-$CF_2ClO$ |
| 3-iPr | 2-$CF_2BrO$ |
| 2-MeO | 3-$CF_2BrO$ |
| 3-MeO | 2-$HCF_2CF_2O$ |
| 2-EtO | 3-$HCF_2CF_2O$ |
| 3-EtO | 2-PhO |
| 2-nPrO | 3-PhO |
| 3-nPrO | 2-$MeOCH_2O$ |
| 2-iPrO | 3-$MeOCH_2O$ |

TABLE 19

| $R^1$–$R^4$ | $R^1$–$R^4$ |
|---|---|
| 2-CN | 3-$CF_3S$ |
| 3-CN | 2-$CF_2HS$ |
| 2-$CH_3S$ | 3-$CF_2HS$ |
| 3-$CH_3S$ | 2-$HC_2F_4S$ |
| 2-EtS | 3-$HC_2F_4S$ |
| 3-EtS | 2-PhO |
| 2-$CF_3S$ | 3-PhO |
|  | 2,6-$Cl_2$ |

Compounds represented by the general formulae

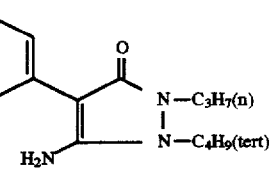

[22]

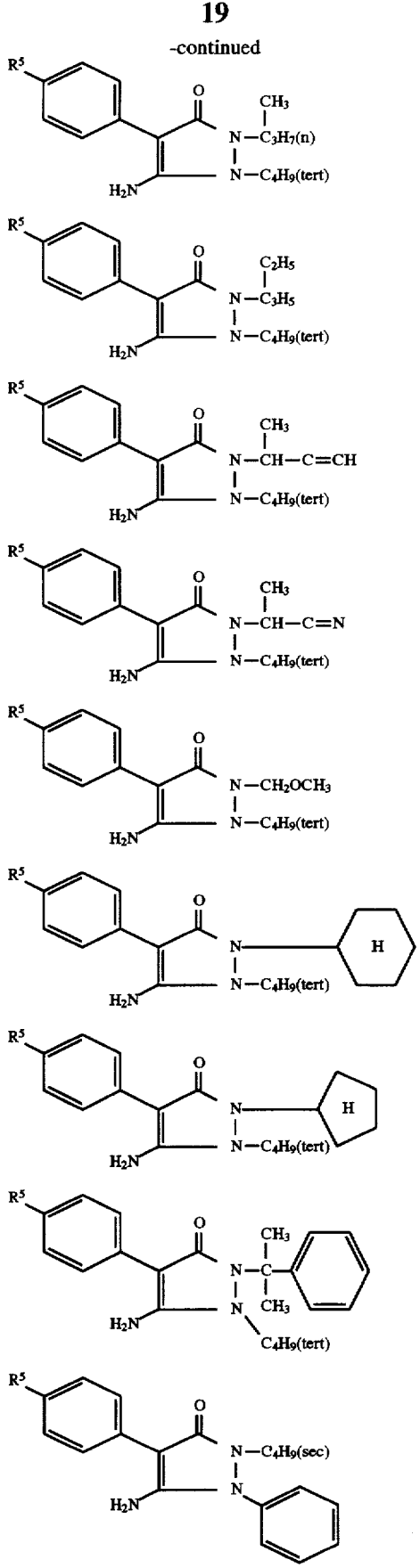
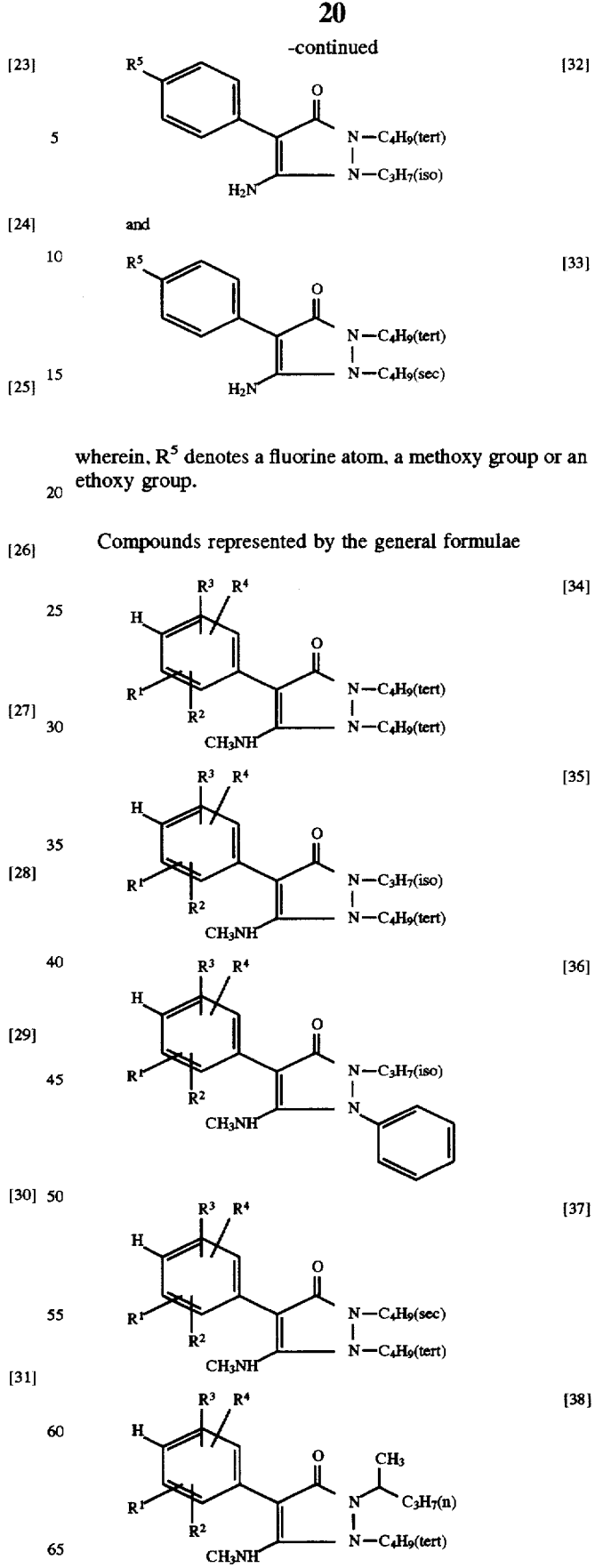
wherein, $R^5$ denotes a fluorine atom, a methoxy group or an ethoxy group.
Compounds represented by the general formulae -continued
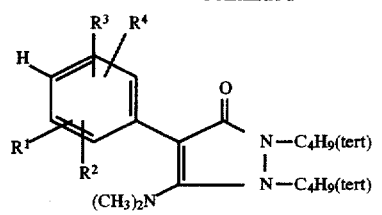 [39]
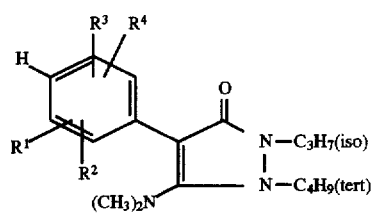 [40]
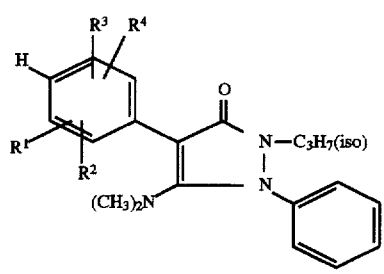 [41]
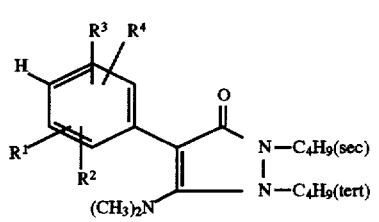 [42]
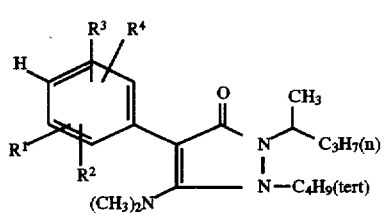 [43]
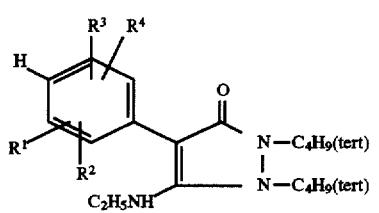 [44]
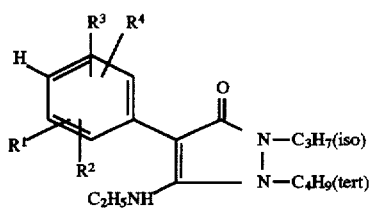 [45]
-continued
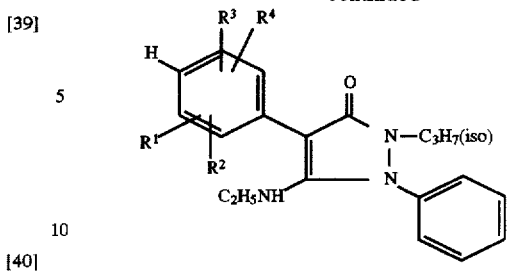 [46]
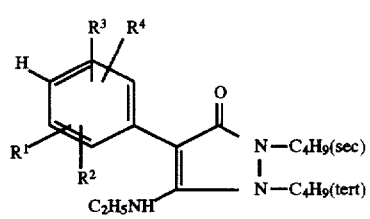 [47]
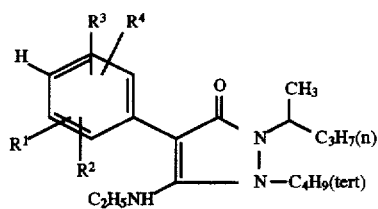 [48]
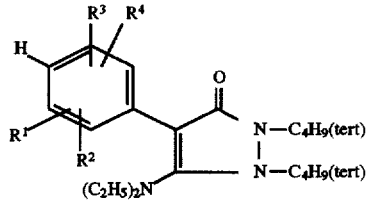 [49]
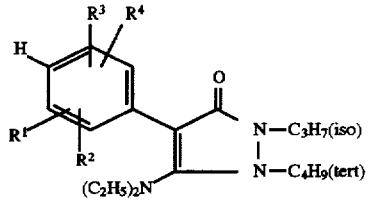 [50]
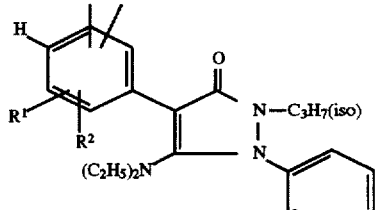 [51]
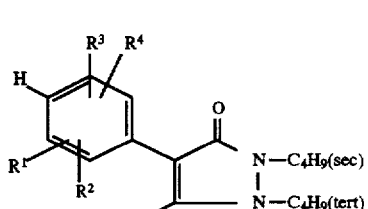 [52]

-continued
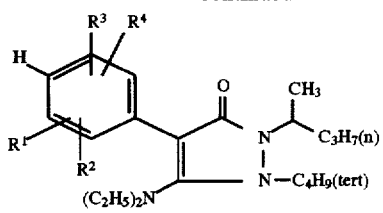 [53]
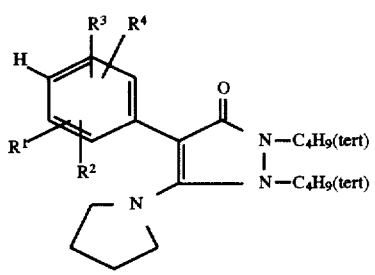 [54]
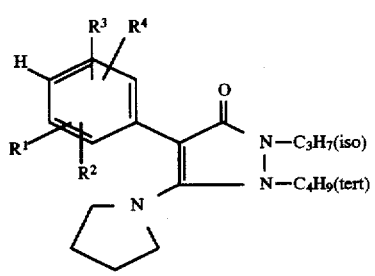 [55]
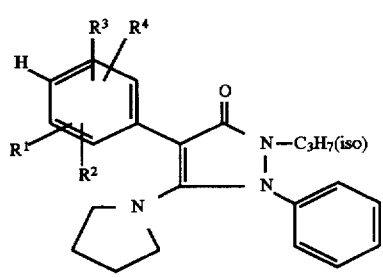 [56]
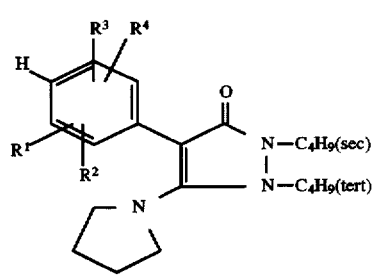 [57]
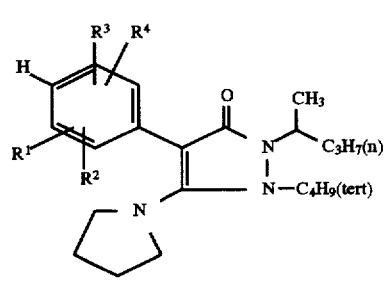 [58]
-continued
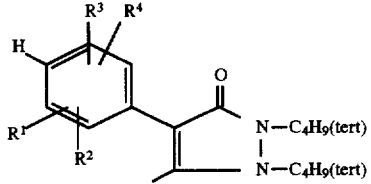 [59]
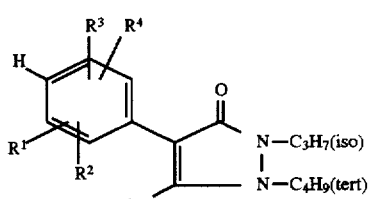 [60]
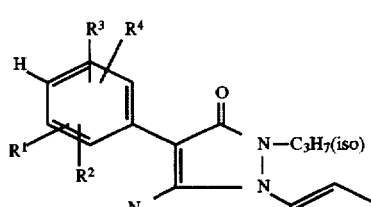 [61]
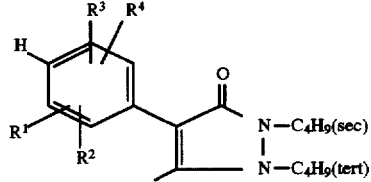 [62]
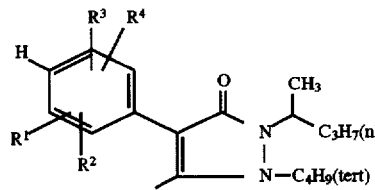 [63]
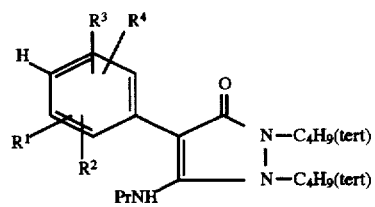 [64]

-continued
[65] 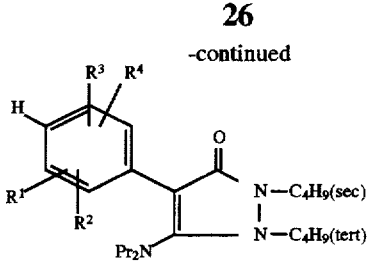
[66]
and
[72] 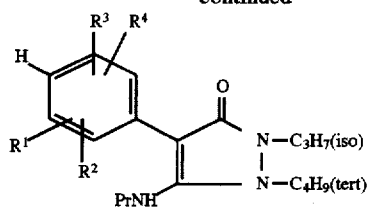
[73] 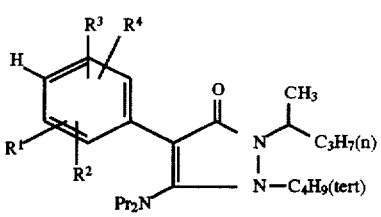
[67] wherein, the substituents of $R^1$ to $R^4$ denote those shown in Table 20.
TABLE 20
| $R^1$–$R^4$ | $R^1$–$R^4$ |
|---|---|
| 2-F | 2-CF$_2$HO |
| 3-F | 3-CF$_2$HO |
| 2-Cl | 2-PhO |
| 3-Cl | 3-PhO |
| 2-Br | 2-CN |
| 3-Br | 3-CN |
| 2-I | 2-PhO |
| 3-I | 3-PhO |
| 2-CH$_3$ | 2,3-F$_2$ |
| 3-CH$_3$ | 2,5-F$_2$ |
| 2-Et | 2,6-F$_2$ |
| 3-Et | 2-F, 3-Cl |
| 2-MeO | 2-F, 5-Cl |
| 3-MeO | 2-F, 6-Cl |
| 2-EtO | 2-F, 3-MeO |
| 3-EtO | 2-F, 5-MeO |
| 2-CF$_3$ | 2-F, 6-MeO |
| 3-CF$_3$ | 2-Cl, 3-F |
| 2-C$_2$F$_5$ | 2-Cl, 5-F |
| 3-C$_2$F$_5$ | 2,3-Cl$_2$ |
| 2-CF$_3$O | 2,5-Cl$_2$ |
| 3-CF$_3$O | 2,6-Cl$_2$ |
[68] 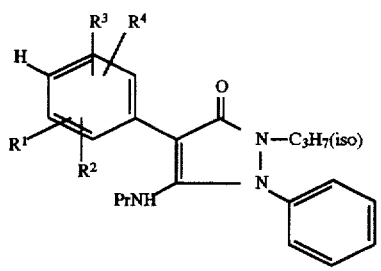
[69] 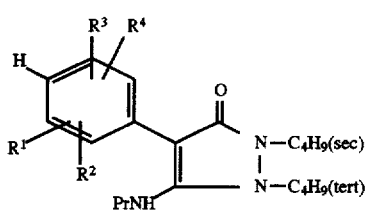
Compounds represented by the general formulae
[70] 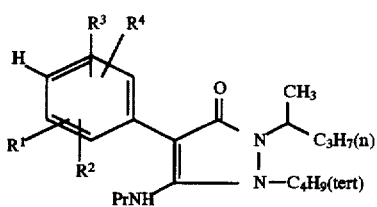
[74] 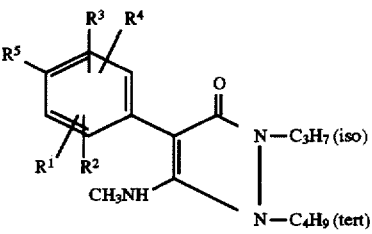
[71] 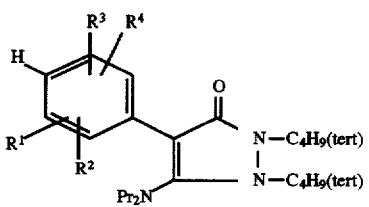
[75] 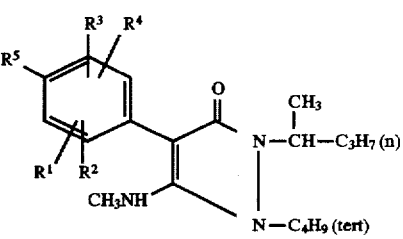
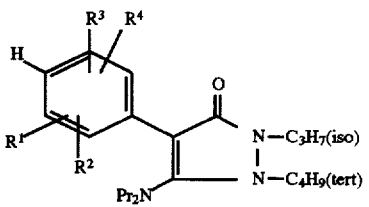
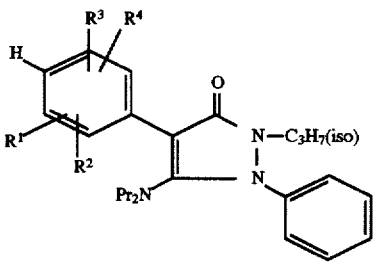

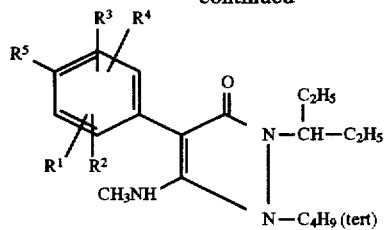 [76]
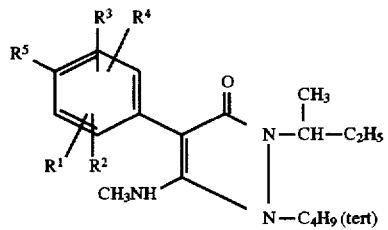 [77]
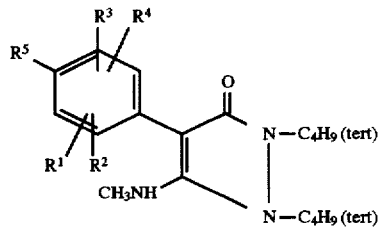 [78]
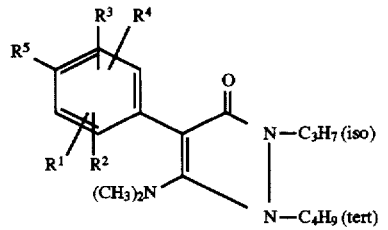 [79]
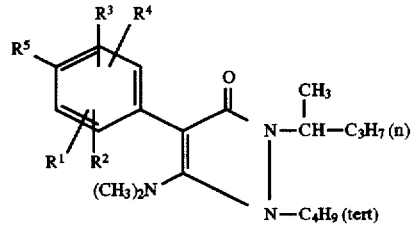 [80]
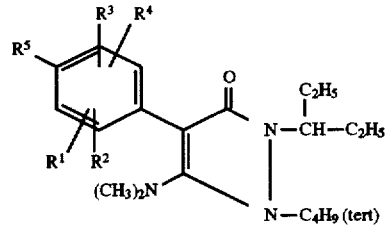 [81]
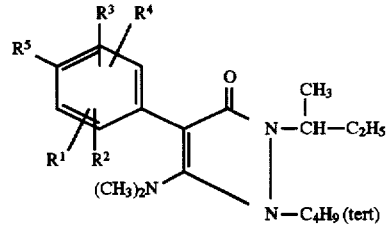 [82]
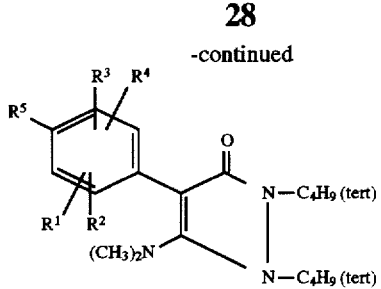 [83]
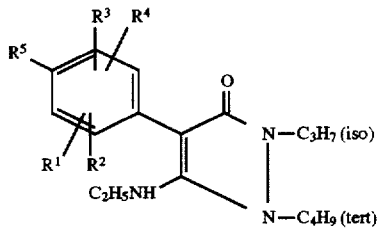 [84]
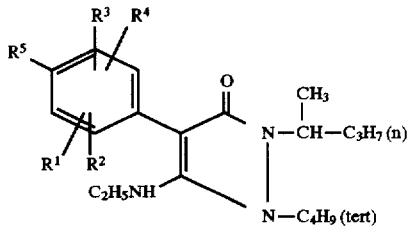 [85]
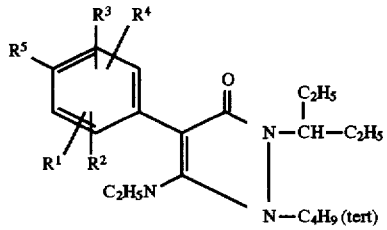 [86]
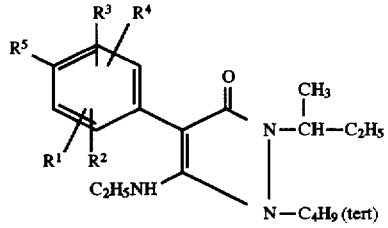 [87]
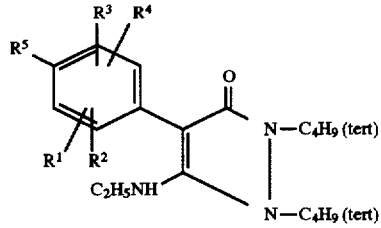 [88]
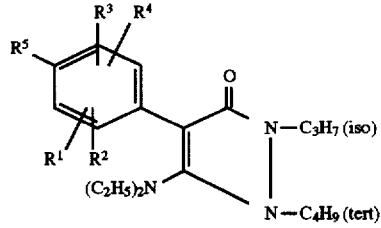 [89]

-continued
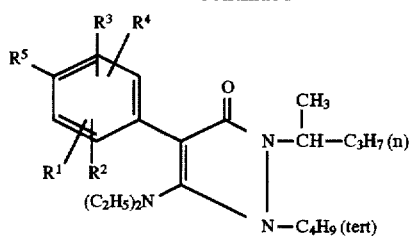 [90]
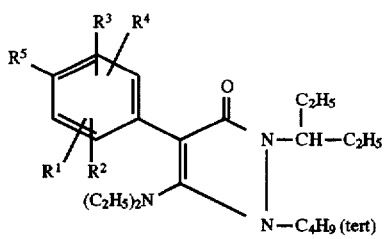 [91]
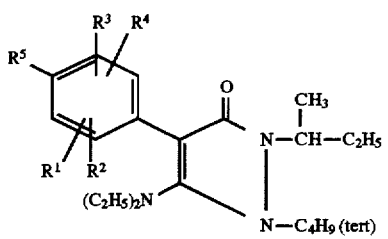 [92]
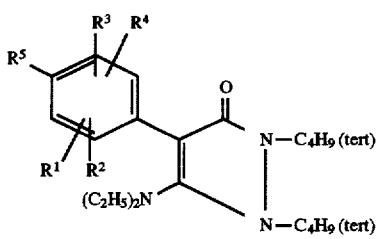 [93]
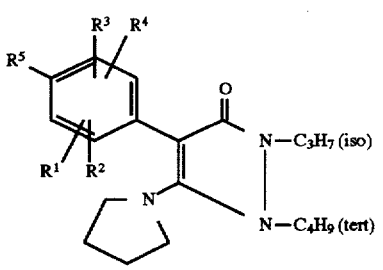 [94]
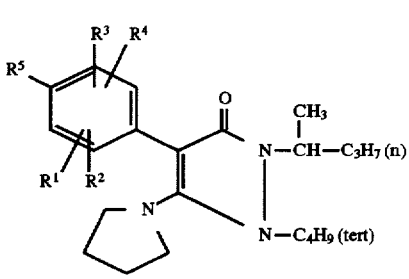 [95]
-continued
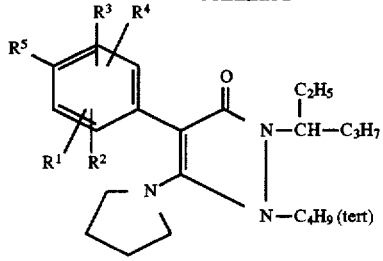 [96]
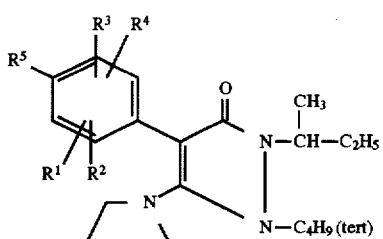 [97]
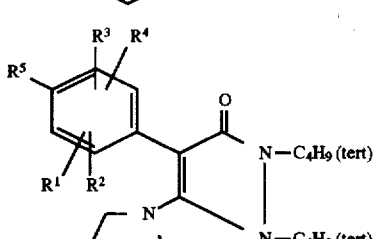 [98]
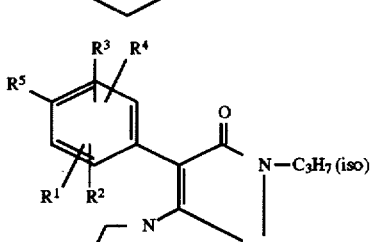 [99]
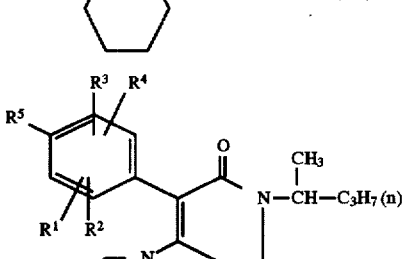 [100]
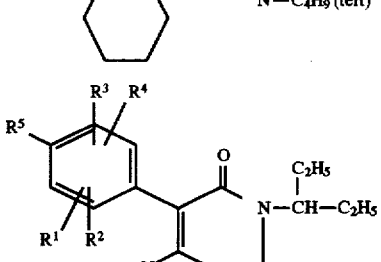 [101]

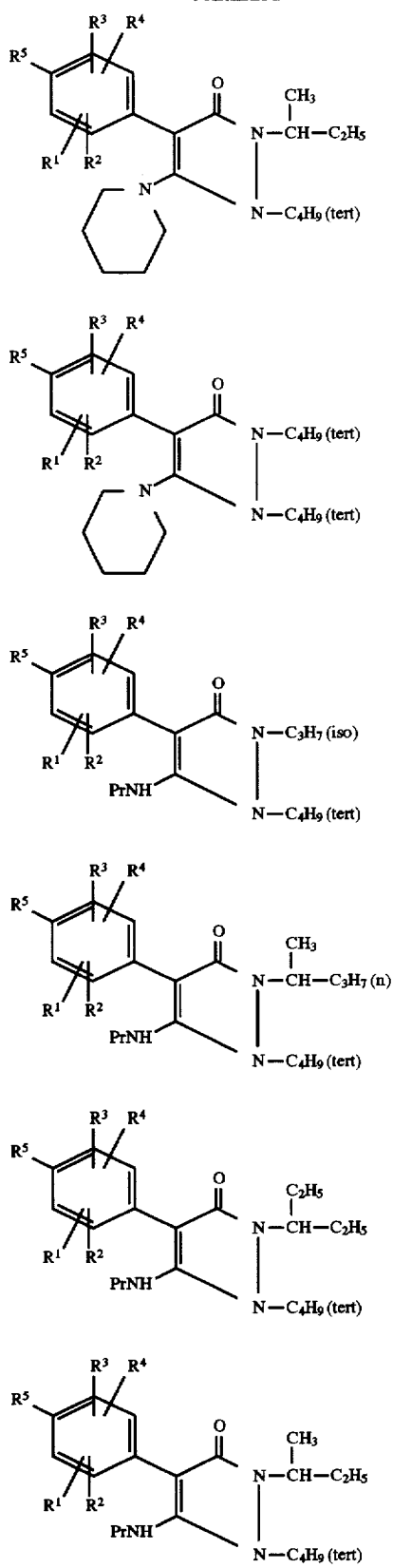
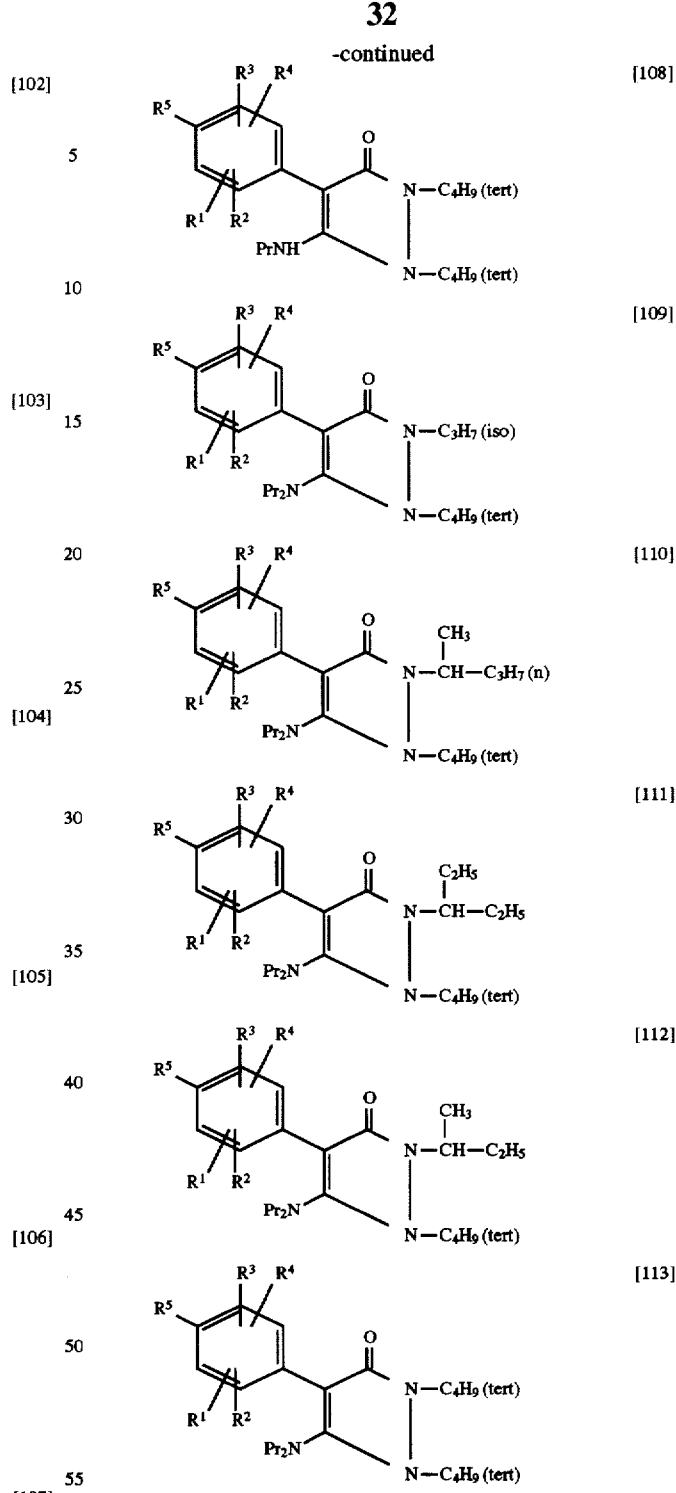
wherein, the substituents of $R^1$ to $R^4$ denote those shown in Table 21, and $R^5$ denotes a fluorine atom, a methoxy group or an ethoxy group.
TABLE 21
| $R^1$–$R^4$ | $R^1$–$R^4$ |
|---|---|
| H | 3-Et |
| 2-F | 3-MeO |
| 2-Cl | 3-EtO |
| 2-Br | 3-$CF_3$ |

TABLE 21-continued
| R¹~R⁴ | R¹~R⁴ |
|---|---|
| 2-CH₃ | 3-CF₃O |
| 2-Et | 3-CF₂HO |
| 2-MeO | 3-CH₃S |
| 2-CF₃ | 3-CF₃S |
| 2-CF₃O | 3-CN |
| 2-CF₂HO | 3-HC₂F₄O |
| 3-F | 3,5-F₂ |
| 3-Cl | 3,5-Cl₂ |
| 3-Br | 3,5-Br₂ |
| 3-CH₃ | 3,5-(CH₃O)₂ |
|  | 2,6-Cl₂ |
Compounds represented by the general formulae
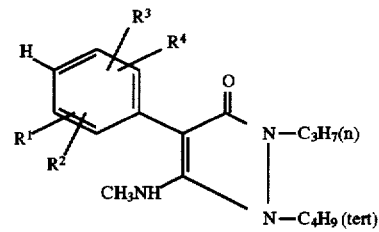  [114]
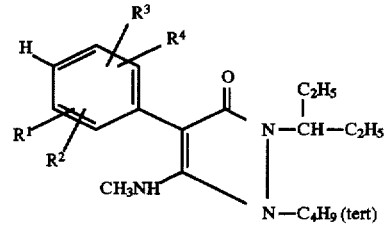  [115]
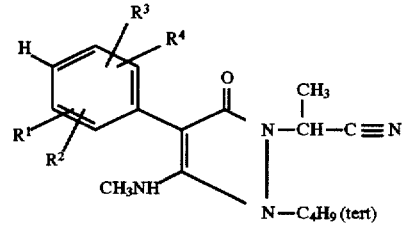  [116]
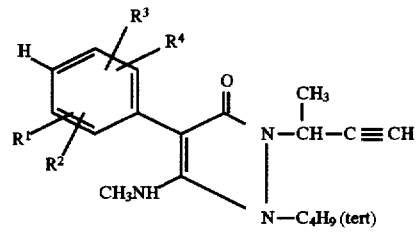  [117]
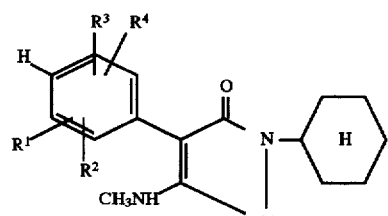  [118]
-continued
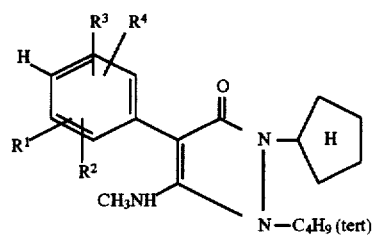  [119]
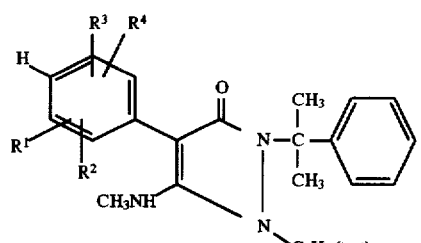  [120]
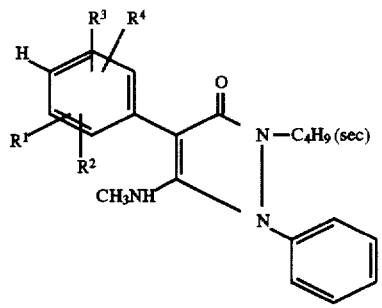  [121]
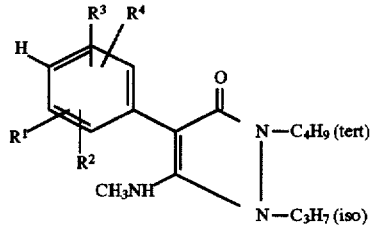  [122]
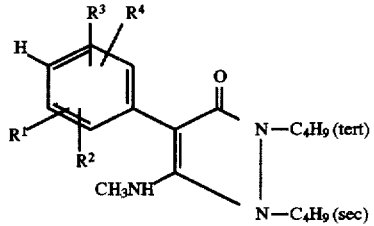  [123]
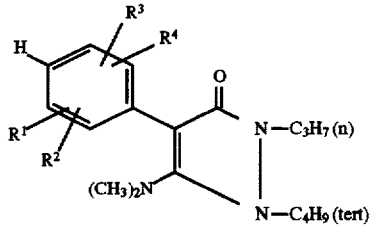  [124]

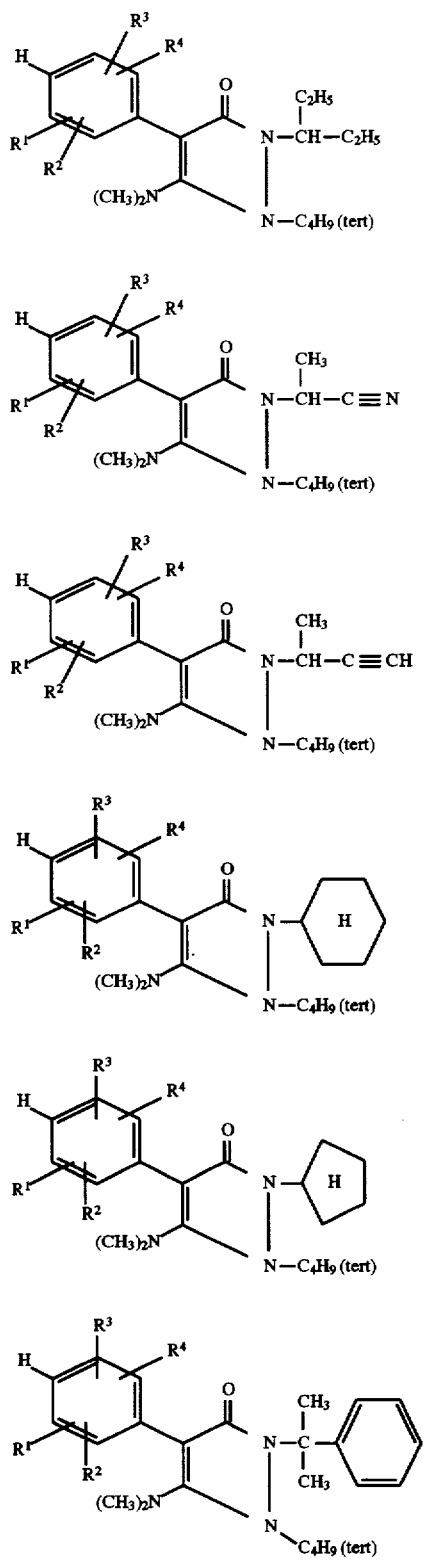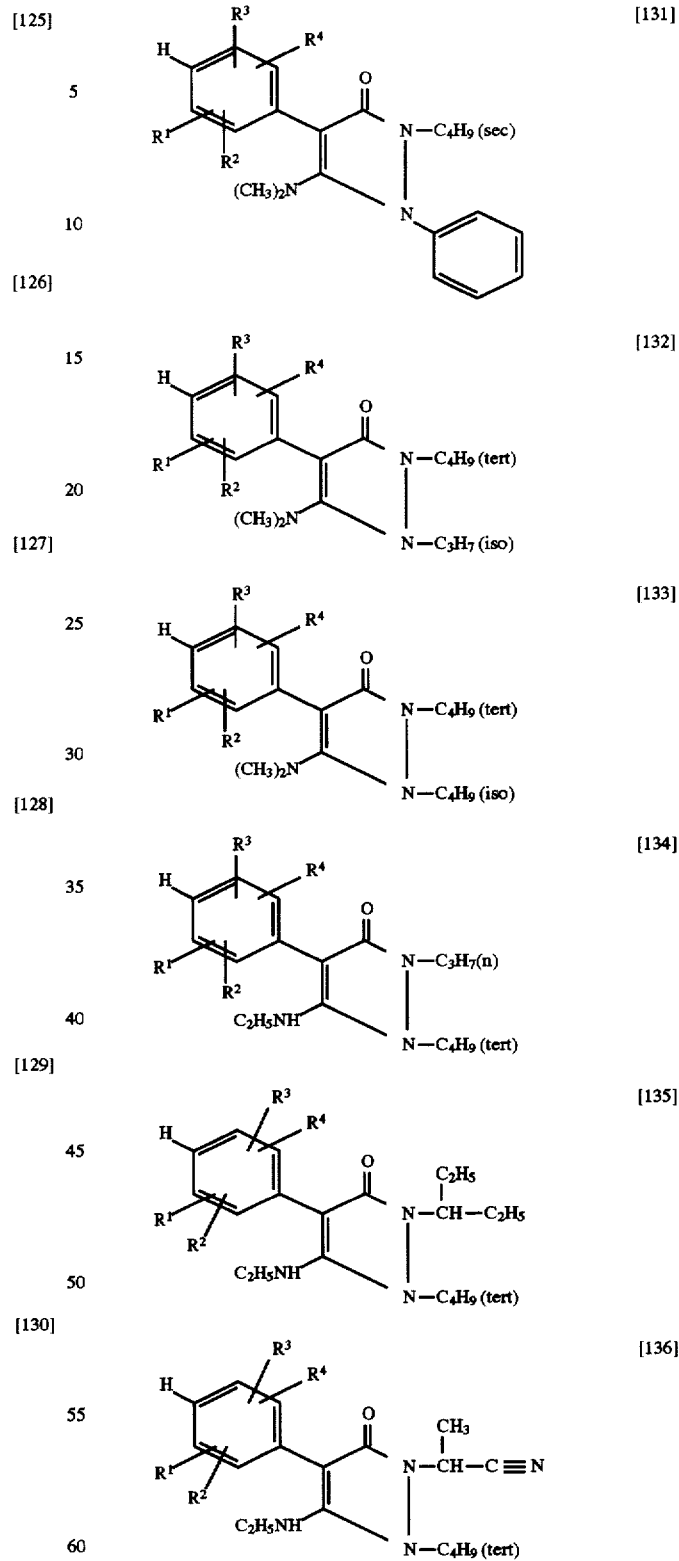

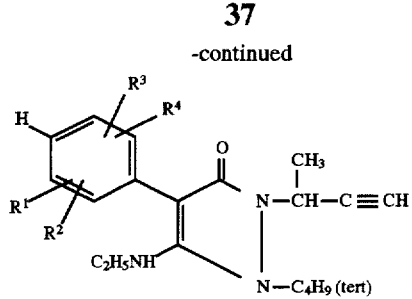 [137]
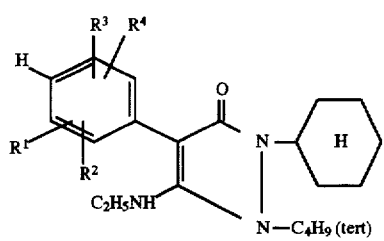 [138]
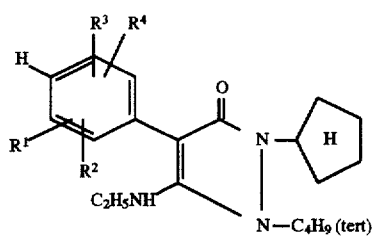 [139]
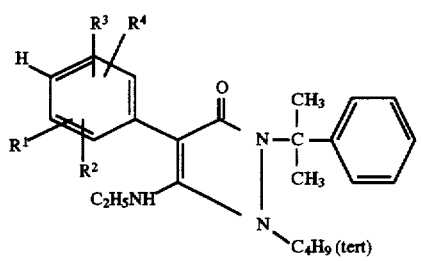 [140]
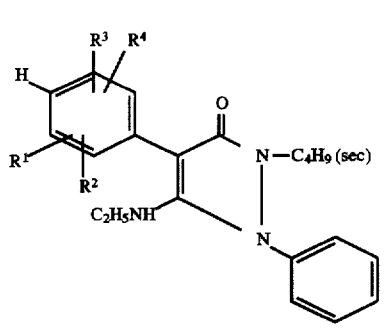 [141]
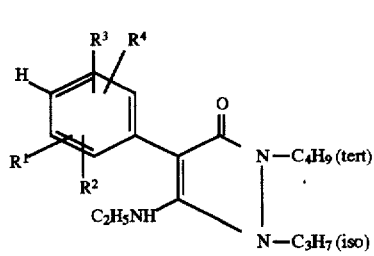 [142]
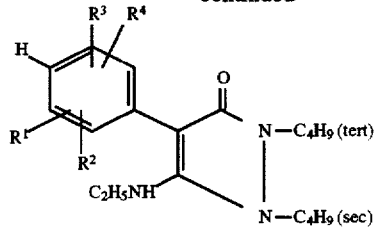 [143]
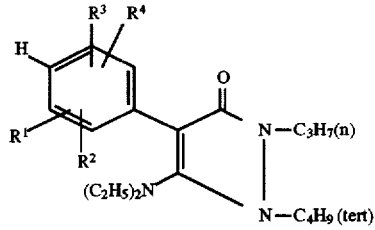 [144]
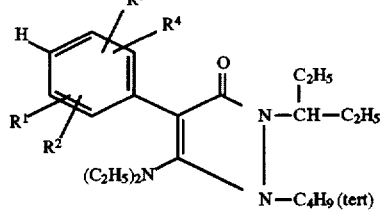 [145]
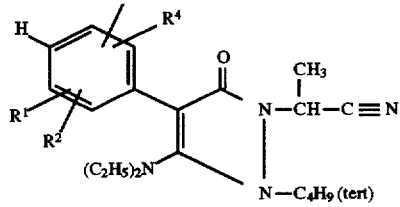 [146]
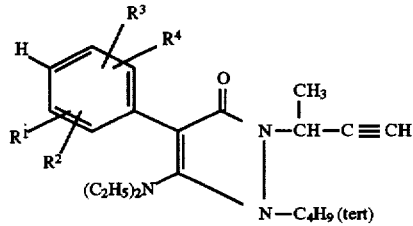 [147]
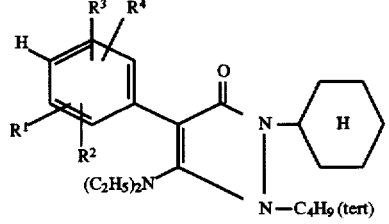 [148]
[149]

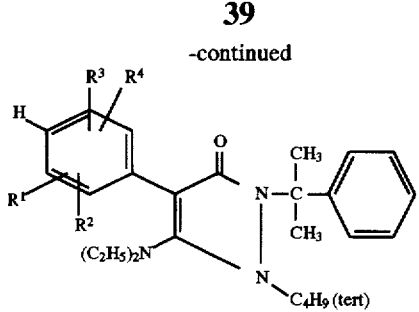
[150]
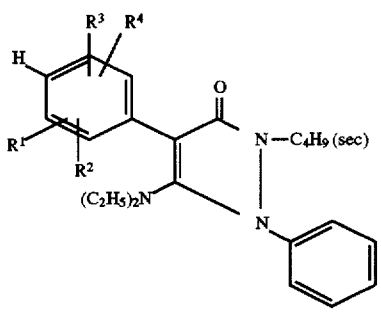
[151]
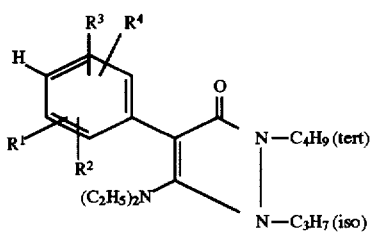
[152]
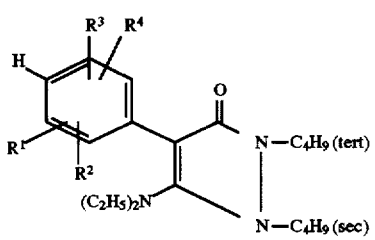
[153]
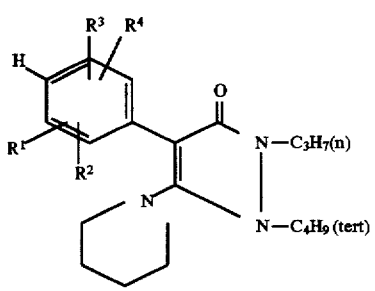
[154]
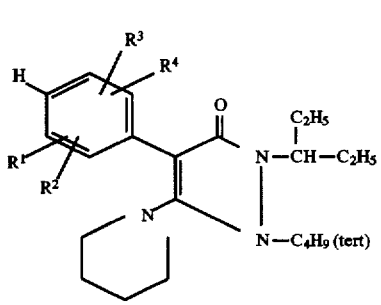
[155]
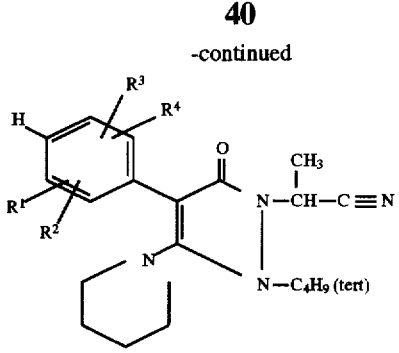
[156]
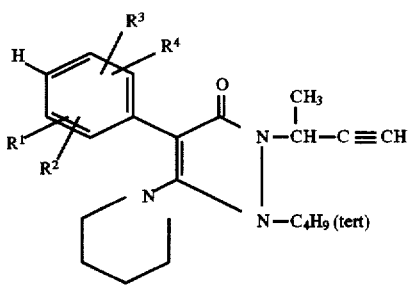
[157]
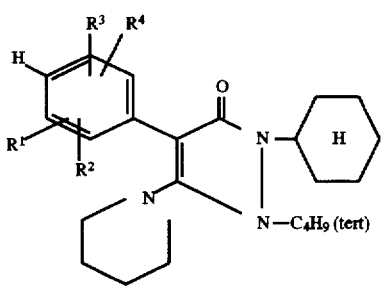
[158]
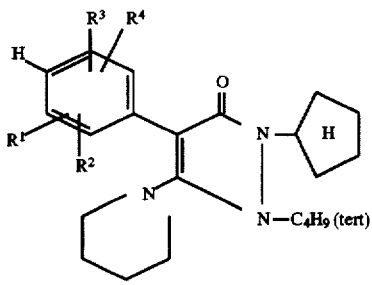
[159]
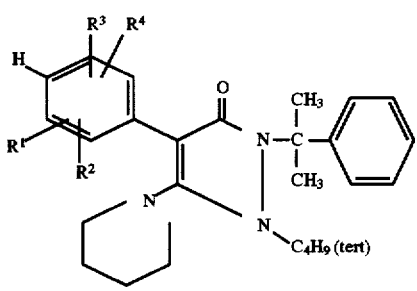
[160]

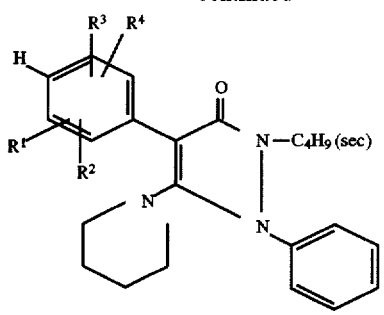
[161]
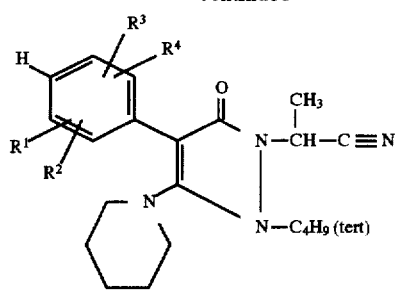
[166]
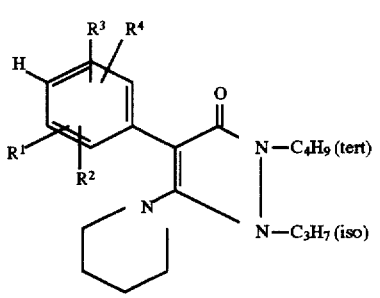
[162]
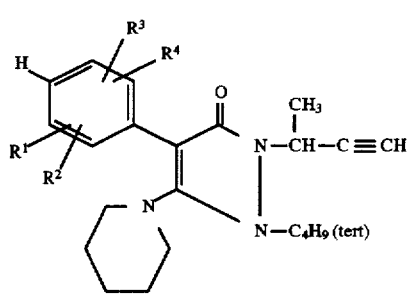
[167]
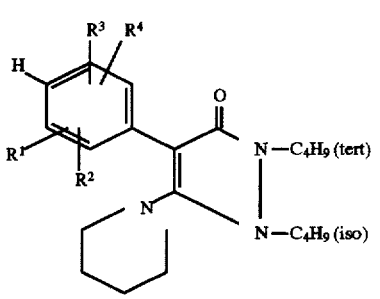
[163]
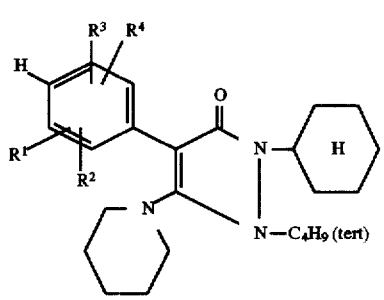
[168]
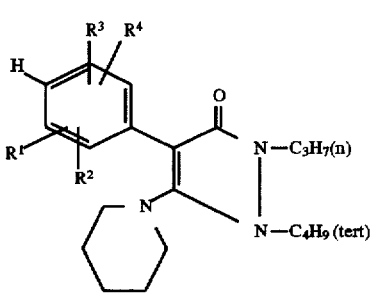
[164]
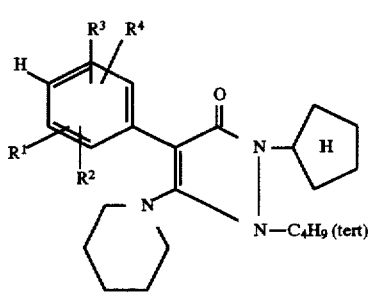
[169]
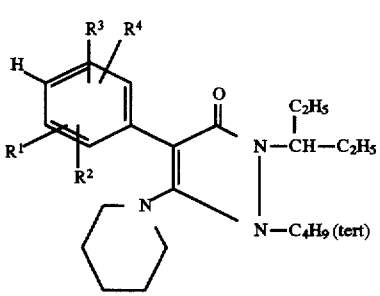
[165]
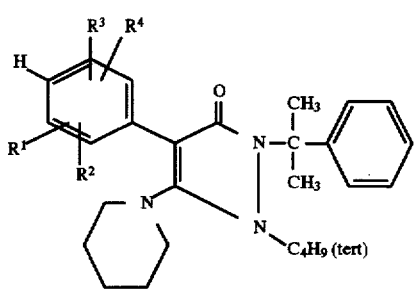
[170]

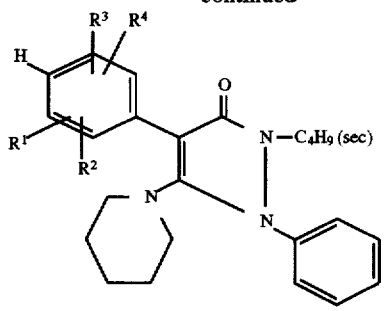
[171]
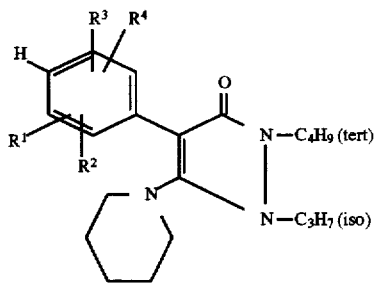
[172]
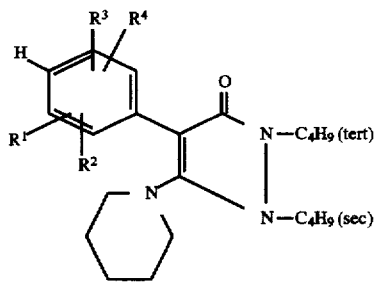
[173]
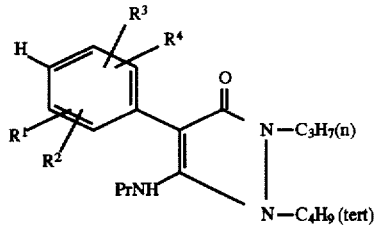
[174]
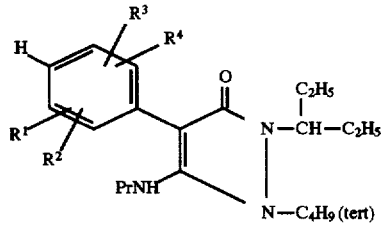
[175]
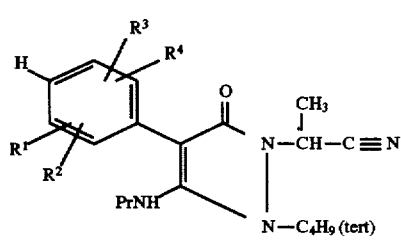
[176]
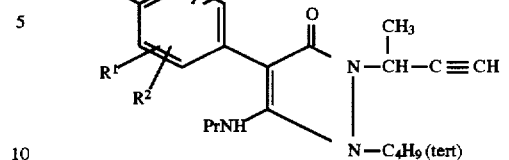
[177]
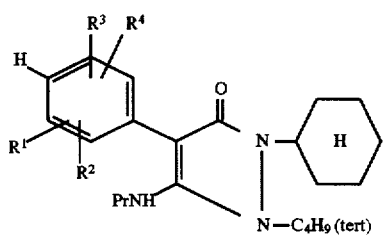
[178]
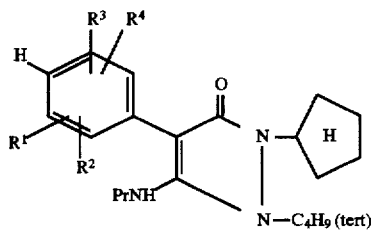
[179]
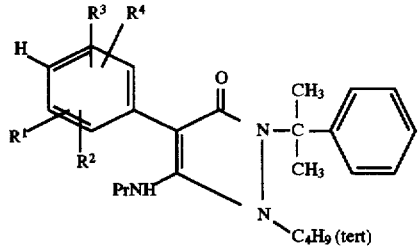
[180]
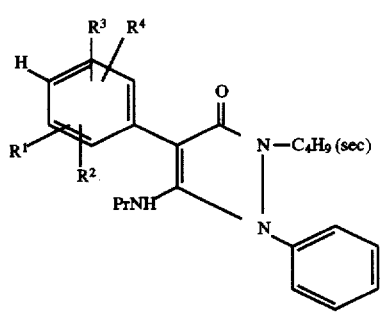
[181]
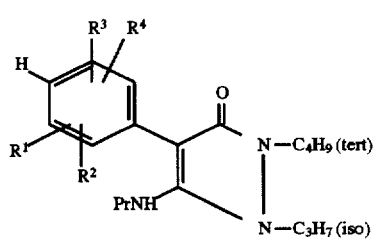
[182]

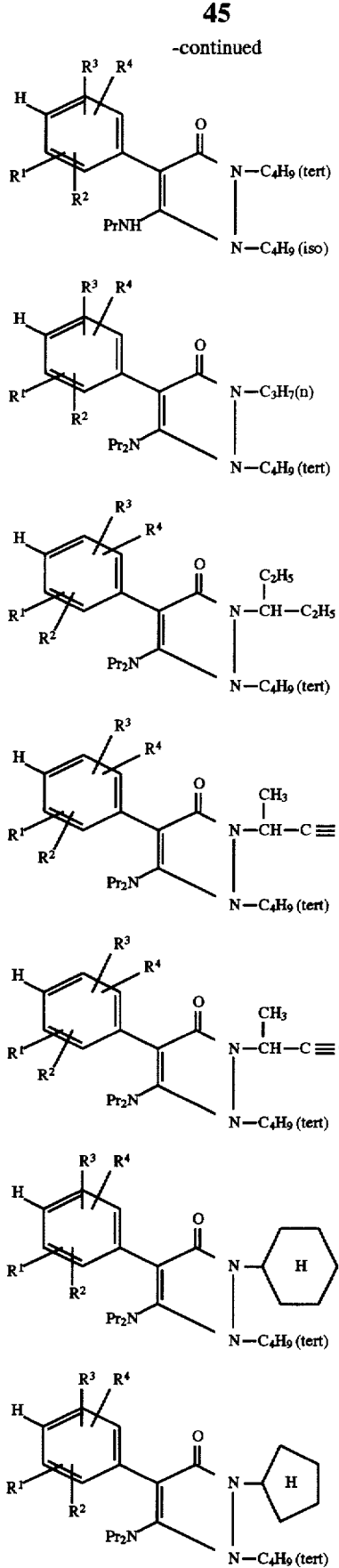
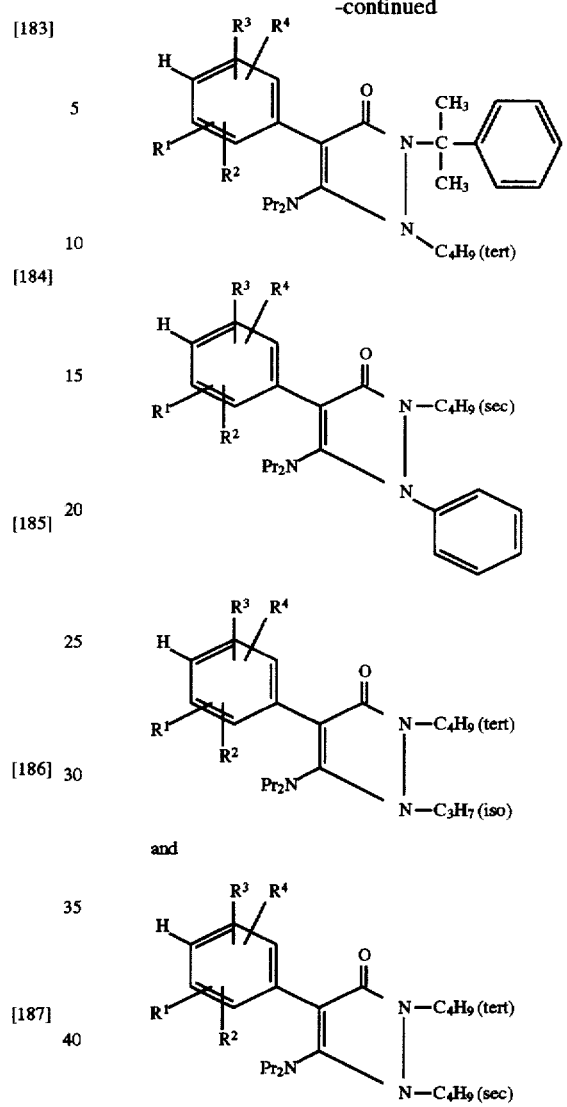
wherein, the substituents of $R^1$ to $R^4$ denote those shown in Table 22 and Table 23.
| TABLE 22 | |
|---|---|
| $R^1$-$R^4$ | $R^1$-$R^4$ |
| 2-F | 3-$C_2F_5$ |
| 3-F | 2-$CF_3O$ |
| 2-Cl | 3-$CF_3O$ |
| 3-Cl | 2-$CF_2HO$ |
| 2-Br | 3-$CF_2HO$ |
| 3-Br | 2-$C_2F_5O$ |
| 2-I | 3-$C_2F_5O$ |
| 3-I | 2-$CF_2ClO$ |
| 2-$CH_3$ | 3-$CF_2ClO$ |
| 3-$CH_3$ | 2-$CF_2BrO$ |
| 2-Et | 3-$CF_2BrO$ |
| 3-Et | 2-$HCF_2CF_2O$ |
| 2-MeO | 3-$HCF_2CF_2O$ |
| 3-MeO | 2-PhO |
| 2-EtO | 3-PhO |
| 3-EtO | 2-MeOCH$_2$O |
| 2-nPrO | 3-MeOCH$_2$O |
| 3-nPrO | 2-CN |
| 2-iPrO | 3-CN |
| 3-iPrO | 2-$CH_3$S |

TABLE 22-continued

| R¹–R⁴ | R¹–R⁴ |
|---|---|
| 2-CF₃ | 3-CH₃S |
| 3-CF₃ | 2-EtS |
| 2-C₂F₅ | 3-EtS |

TABLE 23

| R¹–R⁴ | R¹–R⁴ |
|---|---|
| 2-CF₃S | 2-HC₂F₄S |
| 3-CF₃S | 3-HC₂F₄S |
| 2-CF₂HS | 2-PhO |
| 3-CF₂HS | 3-PhO |

The raw compound of the general formula III used in preparation of the pyrazoline derivative of the general formula I, may be prepared by reacting a phenyl-cyanoacetic ester compound of the general formula VIII.

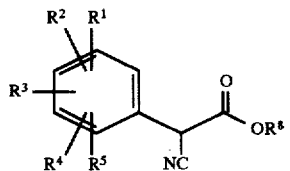

wherein $R^1$ to $R^5$ have the same meanings as in the definitions in the above general formula I, and $R^8$ denotes an alkyl group (e.g., a $C_1$ to $C_4$ alkyl group such as a methyl group and an ethyl group), with, usually 1 to 1.2 equivalents of, a compound of the general formula IX

wherein $R^7$ has the same meaning as in the definition in the above general formula I, usually at 40° to 100° C.

The reaction does not always need a solvent, but can be carried out in a solvent, and usable solvents include alcohols such as methanol and ethanol.

After the completion of the reaction, the reaction mixture can be subjected to usual post-treatments such as organic solvent extraction and/or concentration, and, if necessary, further purified by chromatography, recrystallization, etc. to give the desired compound.

The phenylcyanoacetic ester compounds represented by the general formula VIII may be prepared according to the processes described in Chemistry Letters 193 (1983), J.O.C. 58, 7606 (1993) and Japanese Patent KOKAI No. 1-160, 968.

Specific examples of the pyrazoline compounds of the general formula III are shown below.

Compounds represented by the general formulae

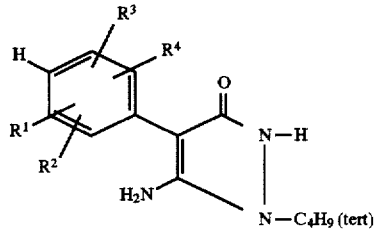

and

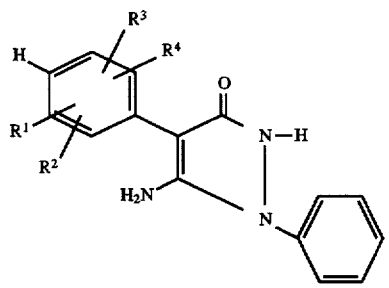

wherein, the substituents of $R^1$ to $R^4$ denote those shown in Table 1 to Table 15.

Compounds represented by the general formulae

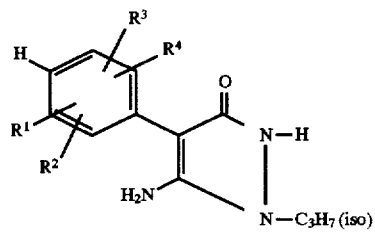

and

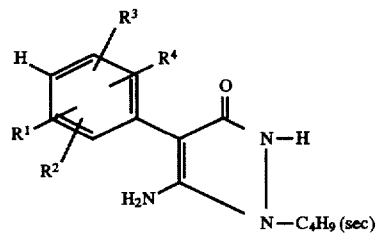

wherein, the substituents of $R^1$ to $R^4$ denote those shown in Table 18 and Table 19.

Compounds represented by the general formulae

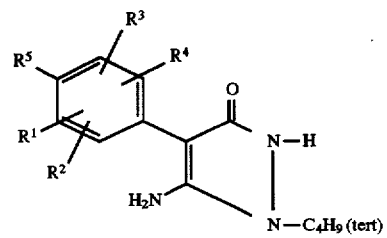

wherein, the substituents of $R^1$ to $R^4$ denote those shown in Table 16 and Table 17, and $R^5$ denotes a fluorine atom, a methoxy group or an ethoxy group.

Compounds represented by the general formulae

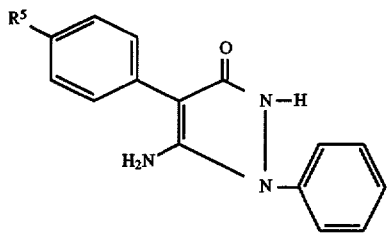

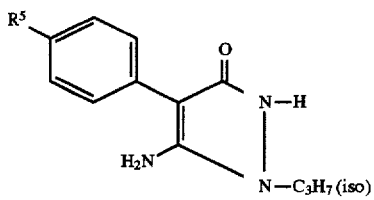

and

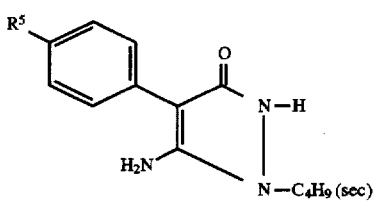

wherein, $R^5$ denotes a fluorine atom, a methoxy group or an ethoxy group.

Plant diseases against which the pyrazoline derivatives of the general formula 5 have efficacy include blast (*Pyricularia oryzae*), Helminthosporium leaf spot (*Cochliobolus miyabeanus*), sheath blight (*Rhizoctonia solani*), powdery mildew (*Erysiphe graminis* f. sp. *hordei*, f. sp. *tritici*), scab (*Gibberella zeae*), rust (*Puccinia striiformis*, *Puccinia graminis, Puccinia recondita, Puccinia hordei*), snow blight (Typhula sp., *Micronectriella nivalis*), loose smuts (*Ustilago tritici, Ustilago nuda*), eye spot (*Pseudocercosporella herpotrichoides*), scald (*Rhynchosporium secalis*), speckled leaf blotches (*Septoria tritici*), glume blotch (*Leptosphaeria nodorum*), Pyrenophora teres, citrus fruit melanose (*Diaporthe citri*), scab (*Elsinoe fawcetti*), Common green mold (*Penicillium digitatum, P. italicum*), apple tree blossom blight (*Sclerotinia mali, Monilinia mali*), apple tree canker (*Valsa mali*), apple brown rot (*Menilinia fructigene*), apple tree powdery mildew (*Podosphaera leucotricha*), Alternaria leaf spot (*Alternaria mali*), apple tree scab (*Venturia inaegualis*), pear tree scab (*Venturia nashicola*), pear tree black spot (*Alternaria kikuchiana*), pear tree rust (*Gymnosporangium haraeanum*), peach tree brown rot (*Sclerotinia cinerea, Menilinia fructicola*), peach tree scab (*Cladosporium carpophilum*), peach tree Phomopsis rot (Phomopsis sp.), vine anthracnose (*Elsino ampelina*), vine ripe rot (*Glomerella cingulate*), vine powdery mildew (*Uncinula nacator*), vine rust (*Phakopsora ampelopsidis*), persimmon tree anthracnose (*Gloeosporium kaki*), persimmon tree angular leaf spot (*Cercospora kaki, Mycosphaerella nawae*), cucurbitaceous anthracnose (*Colletotrichum lagenarium*), cucurbitaceous powdery mildew (*Sphaerotheca fuliginea*), cucurbitaceous gummy stem blight (*Mycosphaerella melonis*), tomato early blight (*Alternaria solani*), tomato leaf mold (*Cladosporium fulvum*), eggplant brown spot (*Phomopsis vexans*), eggplant powdery mildew (*Erysiphe cichoracearum*), Cruciferae vegetable gray leaf spot (*Alternaria japonica*), Cruciferae vegetable white spot (*Cercosporella brassicae*), Welsh onion rust (*Puccinia allii*), soybean purple speck (*Cercospora kikuchii*), soybean Sphaceloma scab (*Elsinoe glycines*), soybean pod and stem blight (*Diaporthe phaseolorum* var. *sajae*), kidney bean anthracnose (*Colletotrichum lindemuthianum*), peanut leaf spot (*Mycosphaerella personnatum*), peanut Cercospora leaf spot (*Cercospora arachidicola*), pea powdery mildew (*Erysiphe pisi*), potato early blight (*Alternaria solani*), strawberry powdery mildew (*Sphaerotheca humuli*), tea plant net blister blight (*Exobasidium reticulatum*), tea plant scab (*Elsinoe leucospila*), tobacco brown spot (*Alternaria longipes*), tobacco powdery mildew (*Erysiphe cichoracearum*), tobacco anthracnose (*Colletotrichum tabacum*), sugar beet Cercospora leaf spot (*Cercospora beticola*), rose black spot (*Diplocarpon rosae*), rose powdery mildew (*Sphaerotheca pannosa*), chrysanthemum leaf blight (*Septoria chrysanthemi-indici*), chrysanthemum rust (*Puccinia horiana*), gray molds of various crop (*Botrytis cinerea*), Botrytis diseases of various crops (Botrytis spp.), Sclerotinia rots of various crop (*Sclerotinia sclerotiorum*), etc.

When the pyrazoline derivative represented by the general formula 5 is used as an effective ingredient of a plant disease-controlling agent, it may be used as such without adding any other component, but usually, the compound is mixed with solid carriers, liquid carriers, surface active agents and other auxiliaries for formulation and made into formulations such as emulsifiable concentrates, wettable powders, suspensions, granules, dusts and liquid formulations.

These formulations contain 0.1 to 99%, preferably 1 to 80% by weight of the pyrazoline derivative as he effective ingredient.

The solid carriers include fine powders or granulates of kaolin clay, attapulgite clay, bentonite, acid clay, pyrophillite, talc, diatom earth, calcite, walnut meal, urea, ammonium sulfate, synthetic hydrated silicon oxide, etc., and the liquid carriers include aromatic hydrocarbons such as xylene and methylnaphthalene, alcohols such as isopropanol, ethylene glycol and cellosolves, ketones such as acetone, cyclohexanone and isophorone, vegetable oils such as soybean oil and cotton seed oil, dimethyl sulfoxide, acetonitrile, water, etc., and the surface active agents used for emulsification, dispersion, wetting, etc. include anionic surface active agents such as alkyl sulfate ester salts, alkyl (aryl) sulfonate salts, dialkylsulfo-succinate salts and polyoxyethylene alkylaryl ether phosphate ester salts, nonionic surface active agents such as polyoxyethylene alkyl ethers, polyoxyethylene alkylaryl ethers, polyoxyethylene polyoxypropylene block copolymers, sorbitan fatty acid esters and polyoxy-ethylene sorbitan fatty acid esters. The auxiliaries for formulation include lignosulfonate salts, alginate salts, polyvinyl alcohol, gum arabic, CMC (carboxymethylcellulose), PAP (isopropyl acid phosphate), etc.

These formulations may be used as such or in various forms, for example, by diluting them with water and applying the dilutions by foliar application, or by applying them through dusting or granule application on the soil and incorporating them into the soil, or merely applying them on the soil, etc. They can also be used for treating seeds. When these formulations are used in mixture with other plant disease-controlling agents, the synergistic control effect can be expected. It is further possible to use these formulations in combination with insecticides, acaricides, nematicides, herbicides, plant growth regulators, fertilizers and/or soil conditioning materials. Other plant protecting agents that can be mixed include, for example, azole-type fungicidal compounds such as propiconazole, triazimenol, prochloraz, penconazole, tebuconazole, flusilazole, diniconazole, bromoconazole, epoxyconazole, difenoconazole, cyproconazole, metconazole, triflumizole, tetraconazole, myclobutanil, fenbuconazole, hexaconazole, fluquinconazole, triticonazole (RPA400717), bitertanol, imazalil and flutriafol;

cyclic amine-type fungicidal compounds such as fenpropimorph, tridemorph and fenpropidin;

benzimidazole-type fungicidal compounds such as carbendazim, benomyl, thiabendazole and thiophanate-methyl; and other compounds such as procymidone, cyprodinil, pyrimethanil, diethofencarb, thiuram, fluazinam, mancozeb, iprodione, vinclozolin, chlorothalonil, captan, mepanipyrim, fenpichlonil, fludioxonil, dichlofluanid, folpet, methyl methoxy-imino-α(o-tolyloxy)-o-tolylacetate, (BAS 490F), (E)-[2-[6-(2-cyanophenoxy)pyrimidin-4-yloxy]phenyl]-3-methoxyacrylate (ICIA 5504) and N-methyl-α-methoxyimino-2-[(2,5-dimethylphenoxy)methyl]phenyl-acetamide.

The pyrazoline derivatives of the general formula I may be used as the effective ingredients of plant disease-controlling agents for paddy fields, plowed fields, orchards, tea plantations, grasslands, lawns, etc.

When the pyrazoline derivative of the general formula I is used as an effective ingredient of a plant disease-controlling agent, its dosage is usually 0.001 to 100 g, preferably 0.01 to 10 g per are, and when the emulsifiable concentrate, the wettable powder, the suspension, the liquid formulation or the like is applied after diluted with water, the application concentration of the pyrazoline derivative is 0.0001 to 1%, preferably 0.001 to 0.1%, and the granules, dusts, etc. may be applied as such without dilution. When the present compounds are used for treating seeds, the amount to be applied is usually 0.001 g to 100 g, preferably 0.01 g to 10 g per 1 Kg of seeds to be treated in terms of the active ingredient.

This invention is described in more detail below according to preparation Examples, Formulation Examples and Test Examples, but this invention is not limited to these examples.

First, preparation Examples of pyrazoline derivatives of the general formula I are described.

Preparation Example 1

560 mg of sodium hydride (60% oil dispersion) was suspended in 10 ml of tetrahydrofuran, and a solution of 1.5 g of 2-chlorophenylacetonitrile in 10 ml of tetrahydrofuran was added dropwise to the suspension under ice cooling. After the mixture was stirred for one hour under ice cooling, a solution of 1.7 g of N,N'-di-tert-butyldiaziridinone in 10 ml of tetrahydrofuran was added dropwise to the mixture. After the dropwise addition, the mixture was stirred at room temperature for 5 hours. Then, 14 ml of 1N hydrochloric acid was added under ice cooling, the mixture was extracted with diethyl ether. The organic layer was dried over anhydrous magnesium sulfate, the solvent was distilled off under reduced pressure, and the residue was subjected to column chromatography to give 500 mg of Compound 3.

Preparation Example 2

A mixture of 1.3 g of 1-tert-butyl-4-(2-chlorophenyl)-5-aminopyrazolin-3-one, 1.3 g of 2-iodopropane, 1.6 g of potassium carbonate and 20 ml of ethanol was refluxed with heating for 10 hours. The solvent was distilled off under reduced pressure, water was added, and the mixture was extracted with ethyl acetate. The organic layer was dried over anhydrous magnesium sulfate, the solvent was distilled off under reduced pressure, and the residue was subjected to column chromatography to give 400 mg of Compound 2.

Preparation Example 3

A mixture of 550 mg of 1,2-di(tert-butyl)-4-(3-bromophenyl)-5-amino-pyrazolin-3-one (Compound 6), 75 mg of tetrabutylammonium bromide, 190 mg of dimethyl sulfate, 0.45 ml of aqueous 45% sodium hydroxide solution and 1.5 ml of dichloromethane was stirred at 25° C. for 40 hours.

After the completion of the reaction, 10 ml each of water and dichloromethane were added to form two layers, the organic layer was dried over anhydrous magnesium sulfate, the solvent was distilled off under reduced pressure, and the residue was subjected to column chromatography to give 310 mg of Compound 77 and 180 mg of Compound 78.

Preparation Example 4

To 160 mg of sodium hydride (60% oil dispersion) was added 30 ml of toluene and 1.00 g of 1-tert-butyl-4-(2,6-dichlorophenyl)-5-amino-pyrazolin-3-one, and the mixture was heated at a temperature of 100° C. for 2 hours. Isopropyl methanesulfonate 550 mg was added to the reaction mixture and heated at a temperature of 100° C. for 3 hours. After the completion of the reaction, water was added to the reaction mixture followed by extraction with ethyl acetate.

The organic layer was dried over anhydrous magnesium sulfate, the solvent was distilled off under reduced pressure, and the residue was subjected to column chromatography to give 355 mg of Compound 28.

Preparation Example 5

A mixture of 1.3 g of 1-tert-butyl-4-(3-chlorophenyl)-5-amino-pyrazolin-3-one, 1.8 g of 2-iodebutane, 2.1 g of potassium carbonate and 20 ml of ethanol was heated at reflux for 10 hours. The solvent was distilled off under reduced pressure, water was added, and the mixture was extracted with ethyl acetate. The organic layer was dried over anhydrous magnesium sulfate, the solvent was distilled off under reduced pressure, and the residue was subjected to column chromatography to give 450 mg of Compound 59.

Preparation Example 6

A mixture of 1.23 g of 1-tert-butyl-4-(2-methylphenyl)-5-amino-pyrazolin-3-one, 1.84 g of 2-iodebutane, 2.1 g of potassium carbonate and 20 ml of ethanol was heated at reflux for 10 hours. The solvent was distilled off under reduced pressure, water was added, and the mixture was extracted with ethyl acetate. The organic layer was dried over anhydrous magnesium sulfate, the solvent was distilled off under reduced pressure, and the residue was subjected to column chromatography to give 250 mg of Compound 33.

Examples of the pyrazoline derivatives of the general formula 5 are shown together with their compound numbers and physical properties in Table 24 to Table 28 (shown by the definitions of the substituents of the pyrazoline derivatives of the general formula 5) and Table 29.

TABLE 24

| Compound No. | R¹~R⁴ | R⁵ | R⁶ | R⁷ | R⁸ | R⁹ | Melting point (°C.) |
|---|---|---|---|---|---|---|---|
| 1 | 2-F | H | tBu | tBu | H | H | 142.1 |
| 2 | 3-F | H | tBu | tBu | H | H | 147.9 |
| 3 | 2-Cl | H | tBu | tBu | H | H | 172.8 |
| 4 | 3-Cl | H | tBu | tBu | H | H | 166.7 |
| 5 | 2-Br | H | tBu | tBu | H | H | 176.5 |
| 6 | 3-Br | H | tBu | tBu | H | H | 158.9 |
| 7 | 3-CH₃ | H | tBu | tBu | H | H | 150.4 |
| 8 | 3-OCH₃ | H | tBu | tBu | H | H | 120.5 |
| 9 | 3-CF₃ | H | tBu | tBu | H | H | 149.9 |
| 10 | 2,3-F₂ | H | tBu | tBu | H | H | 150.6 |
| 11 | 2-F | F | tBu | tBu | H | H | 153.9 |
| 12 | 2,5-F₂ | H | tBu | tBu | H | H | 157.1 |
| 13 | 2,6-F₂ | H | tBu | tBu | H | H | 155.6 |
| 14 | 2-F, 6-Cl | H | tBu | tBu | H | H | 174.2 |
| 15 | 2,3-Cl₂ | H | tBu | tBu | H | H | 164.4 |
| 16 | 2,5-Cl₂ | H | tBu | tBu | H | H | 172.3 |
| 17 | 2,6-Cl₂ | H | tBu | tBu | H | H | 182.8 |
| 18 | 3-F | F | tBu | tBu | H | H | 152.0 |
| 19 | 3,5-F₂ | H | tBu | tBu | H | H | 218.0 |
| 20 | 2-Cl | H | iPr | tBu | H | H | 203.0 |
| 21 | 3-Cl | H | iPr | tBu | H | H | 184.1 |
| 22 | 2-Br | H | iPr | tBu | H | H | 198.7 |
| 23 | 3-Br | H | iPr | tBu | H | H | 174.4 |

TABLE 25

| Compound No. | R¹~R⁴ | R⁵ | R⁶ | R⁷ | R⁸ | R⁹ | Melting point (°C.) |
|---|---|---|---|---|---|---|---|
| 24 | 2-CH₃ | H | iPr | tBu | H | H | 199.7 |
| 25 | 2-OCH₃ | H | iPr | tBu | H | H | 145.7 |
| 26 | 2-CF₃ | H | iPr | tBu | H | H | 190.3 |
| 27 | 2-F, 6-Cl | H | iPr | tBu | H | H | 206.5 |
| 28 | 2,6-Cl₂ | H | iPr | tBu | H | H | 188.6 |
| 29 | 2-Cl | H | iPr | Ph | H | H | 143.8 |
| 30 | 3-Cl | H | iPr | Ph | H | H | 204.3 |
| 31 | 2-Cl | H | sBu | tBu | H | H | 150.3 |
| 32 | 3-Br | H | sBu | tBu | H | H | 154.9 |
| 33 | 2-CH₃ | H | sBu | tBu | H | H | 151.4 |
| 34 | 2-CF₃ | H | sBu | tBu | H | H | 151.8 |
| 35 | 2-F, 6-Cl | H | sBu | tBu | H | H | 161.6 |
| 36 | 2-Cl | H | nPr | tBu | H | H | 113.5 |
| 37 | 2-Cl | H | 1-EtPr | tBu | H | H | 168.1 |
| 38 | 2-Cl | H | c-Hex | tBu | H | H | 192.0 |
| 39 | 2-Cl | H | c-Pent | tBu | H | H | 191.9 |
| 40 | 2-Cl | H | sBu | iPr | H | H | 168.1 |
| 41 | 2,6-Cl₂ | H | sBu | tBu | H | H | 161.6 |
| 42 | 2-Cl | H | iPr | 2-CH₃Ph | H | H | 204.6 |
| 43 | 3-Cl | H | iPr | 2-CH₃Ph | H | H | 178.9 |
| 44 | 2-Cl | H | iPr | 3-CH₃Ph | H | H | *1 |
| 45 | 3-Cl | H | iPr | 3-CH₃Ph | H | H | 193.6 |
| 46 | 2-Cl | H | iPr | 4-CH₃Ph | H | H | 160.9 |

TABLE 26

| Compound No. | R¹~R⁴ | R⁵ | R⁶ | R⁷ | R⁸ | R⁹ | Melting point (°C.) |
|---|---|---|---|---|---|---|---|
| 47 | 3-Cl | H | iPr | 4-CH₃Ph | H | H | 174.3 |
| 48 | 2-Cl | H | iPr | 2-ClPh | H | H | 216.0 |
| 49 | 3-Cl | H | iPr | 2-ClPh | H | H | 194.3 |
| 50 | 2-Cl | H | iPr | 3-ClPh | H | H | *2 |
| 51 | 3-Cl | H | iPr | 3-ClPh | H | H | 200.3 |
| 52 | 2-Cl | H | iPr | 4-ClPh | H | H | 166.0 |
| 53 | 3-Cl | H | iPr | 4-ClPh | H | H | 171.8 |
| 54 | 2-Cl | H | 1-CH₃Bu | tBu | H | H | *3 |
| 55 | 3-Cl | H | 1-CH₃Bu | tBu | H | H | *4 |
| 56 | 2-Cl | H | Et | Ph | H | H | *5 |
| 57 | 3-Cl | H | Et | Ph | H | H | 150.2 |
| 58 | 2-Cl | H | 1-CH₃Propy | tBu | H | H | 179.7 |
| 59 | 3-Cl | H | sBu | tBu | H | H | 143.6 |
| 60 | 3-CF₃ | H | sBu | tBu | H | H | 148.9 |
| 61 | 3-CF₃O | H | sBu | tBu | H | H | 103.7 |
| 62 | 2-Cl, 6-CH₃O | H | iPr | tBu | H | H | *6 |
| 63 | 2-Cl | H | sBu | c-Hex | H | H | 153.6 |
| 64 | 3-Cl | H | sBu | c-Hex | H | H | 152.7 |
| 65 | 2-Et | H | sBu | tBu | H | H | *7 |
| 66 | 3-Cl | H | 1-EtPr | tBu | H | H | 168.3 |
| 67 | 3-Cl | H | 1-CH₃Propy | tBu | H | H | 164.4 |
| 68 | 2-CH₃ | H | 1-CH₃Propy | tBu | H | H | 168.7 |

TABLE 27

| Compound No. | R¹~R⁴ | R⁵ | R⁶ | R⁷ | R⁸ | R⁹ | Melting point (°C.) |
|---|---|---|---|---|---|---|---|
| 69 | 3-Cl | H | Et | tBu | H | H | 150.6 |
| 70 | 2-CH₃ | H | 1-CH₃Bu | tBu | H | H | *8 |
| 71 | 2-CH₃ | H | 1-Et Propy | tBu | H | H | 151.2 |
| 72 | 2-CH₃ | H | 1-CH₃Butyn | tBu | H | H | *9 |
| 73 | 3-CH₃O | CH₃O | sBu | tBu | H | H | 110.3 |
| 74 | 2,3-(CH₃O)₂ | H | sBu | tBu | H | H | 171.4 |
| 75 | 2-CH₃ | H | sBu | tBu | CH₃ | CH₃ | 111.1 |
| 76 | 2-CH₃ | H | sBu | tBu | H | CH₃ | 149.9 |
| 77 | 3-Br | H | tBu | tBu | CH₃ | CH₃ | 108.0 |
| 78 | 3-Br | H | tBu | tBu | H | CH₃ | 152.0 |
| 79 | 2,6-Me₂ | H | sBu | tBu | H | H | *10 |
| 80 | 2,3-Me₂ | H | sBu | tBu | H | H | *11 |
| 81 | H | CH₃O | sBu | tBu | H | H | 151.5 |
| 82 | 2-Ph | H | iPr | tBu | H | H | *12 |
| 83 | 3,5-(CH₃O)₂ | CH₃O | iPr | tBu | H | H | *13 |
| 84 | 2-NO₂ | H | sBu | tBu | H | H | 219.2 |
| 85 | 3-Cl | CH₃O | sBu | tBu | H | H | 171.2 |
| 86 | 3-Cl | H | sBu | tBu | CH₃ | CH₃ | 122.7 |
| 87 | 3-Cl | H | sBu | tBu | H | CH₃ | 176.1 |
| 88 | 2-iPr | H | sBu | tBu | H | H | *14 |
| 89 | 3-Cl | H | tBu | tBu | CH₃ | CH₃ | 118.6 |
| 90 | 3-Cl | H | tBu | tBu | H | CH₃ | 184.2 |

TABLE 28

| Compound No. | R¹~R⁴ | R⁵ | R⁶ | R⁷ | R⁸ | R⁹ | Melting point (°C.) |
|---|---|---|---|---|---|---|---|
| 91 | 3-Cl | H | tBu | tBu | C₂H₅ | C₂H₅ | *15 |
| 92 | 3-Cl | H | tBu | tBu | H | C₂H₅ | *16 |
| 93 | 3-PhO | H | sBu | tBu | H | H | *17 |
| 94 | 2-PhO | H | sBu | tBu | H | H | 168.7 |
| 95 | 2-Cl | H | sBu | 2-ClPh | H | H | *18 |
| 96 | 2-Cl-6-Me | H | sBu | tBu | H | H | *19 |
| 97 | 2,3,6-Cl₃ | H | iPr | tBu | H | H | *20 |
| 98 | 3-Cl | H | tBu | tBu | iPr | H | 126.4 |
| 99 | 2,3-Me₂ | H | iPr | tBu | H | H | 198.9 |
| 100 | 3-CF₃ | H | tBu | tBu | Et | H | 128.1 |
| 101 | 3-Cl | H | sBu | 2-ClPh | H | H | 166.9 |

¹H-NMR (CDCl₃/TMS) δ (ppm)
*1: 7.6–7.2(m, 8H), 4.35–4.1(m, 3H), 2.4(s, 3H), 1.2(d, 6H)
*2: 7.55–7.24(m, 8H), 4.33–4.22(m, 3H), 1.17(d, 6H)

TABLE 28-continued

| Compound No. | $R^1$-$R^4$ | $R^5$ | $R^6$ | $R^7$ | $R^8$ | $R^9$ | Melting point (°C.) |
|---|---|---|---|---|---|---|---|

*3: 7.45–7.19(m, 4H), 4.32(s, 2H), 3.49(m, 1H), 1.86(m, 2H), 1.43–1.17(m, 14H), 0.93(t, 3H)
*4: 7.51–7.15(m, 4H), 4.66(s, 2H), 3.48(m, 1H), 1.92–1.16(m, 16H), 0.90(t, 3H)
*5: 7.58–7.22(m, 9H), 4.26(s, 2H), 3.59(q, 2H), 1.08(t, 3H)
*6: 7.20–6.81(m, 3H), 4.15(s, 2H), 3.74(s, 3H), 3.6(m, 1H), 1.40–1.33(m, 15H)
*7: 7.28–7.05(m, 4H), 4.21(s, 2H), 3.37(m, 1H), 2.51(q, 2H), 2.03–1.83(m, 2H), 1.41–0.90(m, 18H)
*8: 7.28–7.11(m, 4H), 4.21(s, 2H), 3.5(m, 1H), 2.28(s, 3H), 2.0–0.87(m, 19H)
*9: 7.28–6.99(m, 4H), 4.43(s, 2H), 3.6(m, 1H), 2.8–2.6(m, 2H), 2.17(s, 3H), 1.95(t, 1H), 1.46–1.10(m, 12H)
*10: 7.1–7.0(m, 3H), 4.13(s, 2H), 3.48(m, 1H), 2.19(s, 3H), 2.18(s, 3H), 1.93(m, 2H), 1.42(s, 9H), 1.35(d, 3H), 0.94(q, 3H)
*11: 7.07(d, 2H), 6.97(m, 1H), 4.15(s, 2H), 3.35(m, 1H), 2.28(s, 3H), 2.14(s, 3H), 1.90(m, 2H), 1.40(s, 9H), 1.26(d, 3H), 0.92(q, 3H)
*12: 7.45–7.20(m, 9H), 3.72(s, 2H), 3.55(m, 1H), 1.36(d, 6H), 1.20(s, 9H)
*13: 6.70(s, 2H), 4.62(s, 2H), 3.86(s, 6H), 3.82(s, 3H), 3.62(m, 1H), 1.40(s, 9H), 1.36(d, 6H)
*14: 7.4–7.0(m, 4H), 4.12(s, 2H), 3.35(m, 1H), 3.05(m, 1H), 1.85(m, 2H), 1.40(s, 9H), 1.25(m, 6H), 1.11(d, 3H), 0.93(q, 3H)
*15: 7.26–7.05(m, 4H), 3.95–2.6(m, 4H), 1.26(s, 9H), 1.24–1.22(m, 12H), 1.01(t, 3H)
*16: 7.3–7.2(m, 4H), 4.4–4.3(m, 1H), 3.17–3.07(m, 2H), 1.31(s, 9H), 1.30(s, 9H), 1.15(t, 3H)
*17: 7.33–6.98(m, 9H), 4.61(s, 2H), 3.35(m, 1H), 1.9(m, 2H), 1.38(s, 9H), 1.28(d, 2H), 0.90(t, 3H)
*18: 7.55–7.22(m, 8H), 4.21(s, 2H), 4.05–3.97(m, 1H), 1.88–0.78(m, 8H)
*19: 7.4–7.0(m, 3H), 4.3(s, 2H), 2.2(s, 3H), 1.4(s, 9H)
*20: 7.45–7.1(m, 2H), 4.2(s, 2H), 3.71–3.60(m, 1H), 1.45–1.39(m, 15H)

In the above Tables 24 to 28, tBu represents a tert-butyl group, iPr an isopropyl group, Ph a phenyl group, sBu a sec-butyl group, nPr a n-propyl group, 1-EtPr a 1-ethylpropyl group, c-Hex a cyclohexyl group, c-Pent a cyclopentyl group, Propy a 2-propynyl group, and Butyn a 3-butynyl group, respectively.

TABLE 29

| Compound No. | Structural formula | Melting point (°C.) |
|---|---|---|
| 101 | | 209.3 |
| 102 | | 154.0 |
| 103 | | 164.3 |
| 104 | | 176.3 |
| 105 | | 173.5 |
| 106 | | 154.2 |
| 107 | | *21 |
| 108 | | *22 |

*21: $^1$H-NMR(CDCl$_3$TMS)δ(ppm)7.15–7.1(m, 2H), 1.38(s, 9H), 7.05–6.95 (m, 1H), 1.37(d, 6H), 4.34(s, 2H), 3.62(m, 1H), 2.92(t, 2H), 2.85(t, 2H), 2.06(t, 2H)
*22: 7.15–6.90(m, 3H), 4.2(s, 2H), 3.6(m, 1H), 3.0–2.7(m, 4H), 1.85–1.70(m, 4H), 1.39(s, 9H), 1.29(d, 6H)

A preparation Example of the pyrazoline compounds represented by the general formula VII is shown below.

Preparation Example of an intermediate

To 3.1 g of tert-butylhydrazine hydrochloride was added 4.8 g of 28% sodium methylate methanol solution, followed by stirring at room temperature for 30 minutes. The precipitated salt was filtered out by suction filtration, 5.6 g of ethyl 2-chlorophenyl-cyanoacetate was added to the filtrate, and the mixture was refluxed with heating for 2 hours. The solvent was distilled off and the residue was washed with diethyl ether to give 4 g of 1-tert-butyl-4-(2-chlorophenyl)-5-aminopyrazolin-3-one.

Some examples of the pyrazoline compounds represented by the general formula VII are shown together with 1H-NMR data in Table 30 and Table 31 (shown by the definitions of the substituents of the pyrazoline compounds represented by the general formula VII).

TABLE 30

| $R^1$–$R^4$ | $R^5$ | $R^7$ | $^1$H-NMR (DMSO-$d_6$) δ (ppm) |
|---|---|---|---|
| 2-CH$_3$ | H | tBu | 9.1(s, 1H), 7.16–7.12(m, 4H), 4.79 (s, 2H), 2.18(s, 3H), 1.41(s, 9H) |
| 2-Cl | H | tBu | 9.1(s, 1H), 7.5–7.15(m, 4H), 4.91 (s, 2H), 1.42(m, 9H) |
| 2-OCH$_3$ | H | tBu | 9.15(s, 1H), 7.3–6.85(m, 4H), 4.70 (s, 2H), 3.76(s, 3H), 1.43(s, 9H) |
| 2-Cl | H | Ph | 9.95(s, 1H), 7.6–7.2(m, 9H), 5.3(s, 2H) |
| 2-CF$_3$ | H | tBu | 9.1(s, 1H), 7.72(d, 1H), 7.62(t, 1H), 7.49(t, 1H), 7.22(d, 1H), 4.90 (s, 2H), 1.37(s, 9H) |
| 2-Br | H | tBu | 9.2(s, 1H), 7.63(d, 1H), 7.4–7.1(m, 3H), 4.91(s, 2H), 1.41(s, 9H) |
| 2-C$_2$H$_5$ | H | tBu | 9.10(s, 1H), 7.22–7.04(m, 4H), 4.76 (s, 2H), 2.49(q, 2H), 1.39(s, 9H), 1.02(t, 3H), 8.2(s, 1H) |

TABLE 31

| $R^1$–$R^4$ | $R^5$ | $R^7$ | $^1$H-NMR (DMSO-$d_6$) δ (ppm) |
|---|---|---|---|
| 3-Cl | CH$_3$O | tBu | 7.45(s, 1H), 7.3(d, 1H), 7.08(d, 1H), 5.10(s, 2H), 3.8(s, 3H), 1.42(s, 9H) |
| H | CH$_3$O | tBu | 8.3(s, 1H), 7.33(d, 2H), 6.88(d, 2H), 4.9(s, 2H), 3.72(s, 3H), 1.40(s, 9H) |
| 2-Cl | H | iPr | 9.16(s, 1H), 7.45–7.19(m, 4H), 5.69 (s, 2H), 4.16(m, 1H), 1.16–1.13(d, 6H) |
| 3-Cl | H | iPr | 9.54(s, 1H), 7.64–7.03(m, 4H), 6.00 (s, 2H), 4.28(m, 1H), 1.15–1.13(d, 6H) |
| 3-Cl | H | tBu | 9.55(s, 1H), 7.52–7.11(m, 4H), 5.21 (s, 2H), 1.45(s, 9H) |
| 3-Br | H | tBu | 9.59(s, 1H), 7.68(s, 1H), 7.47–7.27 (m, 3H), 5.22(s, 2H), 1.46(s, 9H) |
| 2,6-Cl$_2$ | H | tBu | 9.1(s, 1H), 7.45–7.15(m, 3H), 5.0 (s, 2H), 1.42(s, 9H) |

In Table 30 and Table 31, tBu represents a tert-butyl group, iPr an isopropyl group,and Ph a phenyl group.

Formulation Examples are shown below. The compounds are shown by the compound numbers in Table 24 to Table 29. The parts mean weight parts.

Formulation Example 1

50 parts each of Compounds 1 to 109, 3 parts of calcium lignosulfonate, 2 parts of sodium lauryl sulfate and 45 parts of synthetic hydrated silicon oxide are well ground and mixed respectively to give respective wettable powders.

Formulation Example 2

10 parts each of Compounds 1 to 109, 14 parts of polyoxyethylene styryl phenyl ether, 6 parts of calcium dodecylbenzenesulfonate and 70 parts of xylene are well mixed respectively to give respective emulsifiable concentrates.

Formulation Example 3

2 parts each of Compounds 1 to 109, 1 part of synthetic hydrated silicon oxide, 2 parts of calcium lignosulfonate, 30 parts of bentonite and 65 parts portions of kaolin clay are well ground and mixed, well kneaded with addition of water, and granulated and dried, respectively to give respective granules.

Formulation Example 4

25 parts each of Compounds 1 to 109, 3 parts of polyoxyethylene sorbitan monooleate, 3 parts of CMC and 69 parts of water are mixed, and wet-ground until the particle size of each effective ingredient becomes 5 microns or less, respectively to give respective suspensions.

Formulation Example 5

10 parts each of Compounds 1 to 109, 1 part of polyoxyethylene styryl phenyl ether, 89 parts of water are mixed respectively to give respective liquid formulations.

It is exhibited by test examples that the pyrazoline derivatives of the general formula I are useful as an effective ingredient of plant disease-controlling agents. The pyrazoline derivatives are specified by the compound numbers in Table 24 to Table 29.

Fungicidal activities were judged by observing with the naked eye the pathopoiesis states of the test plants at the time of investigation, namely the degrees of mycelial tufts and lesions on the leaves and the stems,etc., and determining pathopoiesis degrees from the lesion area rates.

Test Example 1

Cucumber gray mold control test (preventive effect)

Portions of sandy loam were filled into 90-ml plastic pots respectively, and cucumbers (Sagami hanjiro) were sowed and cultivated respectively in a greenhouse for 10 days. 500 ppm water suspensions of each of Compounds 1, 3, 5, 13, 14, 17, 20, 22, 24, 25, 26, 27, 28, 29, 31, 33, 34, 35, 37, 40, 41, 54, 58, 63, 65, 68, 70, 71, 72, 79, 80, 96, 99, 102 and 105 made into formulations in the same manner as in Formulation example 4 were applied, respectively, by foliar application on the surfaces of the leaves of the cucumber young seedlings in which cotyledons were developed, so that the water suspensions could sufficiently deposit thereon. After the chemical liquids were air dried, portions of a PDA medium containing the hyphae of Botrytis cinerea were inoculated on the cotyledon surfaces of the cucumber young seedlings, respectively, the systems were held at 15° C. for 4 days under darkness and much moisture, and then the degrees of pathopoiesis were investigated. As a result, the pathopoiesis degree in the untreated section was 100%, whereas the pathopoiesis degrees in all the sections treated with the above compounds were under 10%.

Test Example 2

Wheat powdery mildew control test (curative effect)

Portions of sandy loam were filled into 90-ml plastic pots respectively, and wheats (Norin No. 73) were sowed and cultivated respectively in a greenhouse for 10 days. Spores of Erysiphe graminis f. sp. tritici were inoculated by sprinkling on the resultant wheat young seedlings in each of which the second leaf was developed. After the inoculation, the young seedlings were raised for 2 days in a growth chamber of 15° C., and 500 ppm aqueous solutions of each of Compounds 1, 2, 3, 4, 5, 6, 7, 8, 9, 10, 12, 14, 15, 16, 18, 21, 23, 25, 29, 30, 32, 33, 43, 49, 53, 55, 59, 66, 73, 77, 78, 81, 85, 86, 89, 90, 91, 92, 95, 96, 98, 101 and 102 made into formulations in the same manner as in Formulation example 2 were applied, respectively, by foliar application on the surfaces of the leaves of the wheat young seedlings, so that the aqueous solutions sufficiently deposit thereon. After the application, the young seedlings were raised for 10 days in a growth chamber of 15° C., and then the degrees of pathopoiesis were investigated.

As a result, the pathopoiesis degree in the untreated section was 100%, whereas the pathopoiesis degrees in all the sections treated with the above compounds were under 10%.

Test Example 3

Wheat powdery mildew control test (systemic effect)

Portions of sandy loam were filled into 90-ml plastic pots respectively, and wheats (Norin No. 73) were sowed and cultivated respectively in a greenhouse for 10 days. Water suspensions of each of Compounds 1, 2, 3, 4, 5, 6, 7, 8, 9, 10, 12, 13, 14, 15, 16, 18, 20, 21, 22, 23, 25, 28, 29, 30, 31, 32, 33, 34, 35, 37, 41, 43, 46, 52, 53, 55, 57, 59, 60, 65, 66, 67, 68, 69, 70, 71, 72, 73, 74, 76, 79, 80, 81, 85, 86, 96, 98, 100, 101, 102, 104, 105 and 106 made into formulations in the same manner as in Formulation example 4 were drenched at the plant feet of the wheat young seedlings in each of which the second leaf was developed, so that the amounts of the effective ingredients became 2.5 mg per pot, respectively. After the treatment, the wheat young seedlings were held for 5 days in a greenhouse of 24° C. and then inoculated by sprinkling with spores of Erysiphe graminis f. sp. tritici. After the inoculation, the wheat young seedlings were held for 10 days in a growth chamber of 15° C., and then the degrees of pathopoiesis were investigated. As a result, the pathopoiesis degree in the untreated section was 100%, whereas the pathopoiesis degrees in all the sections treated with the above compounds were under 10%.

Test Example 4

Kidney bean Sclerotinia rot control test (preventive effect)

Portions of sandy loam were filled into 130-ml plastic pots respectively, and kidney beans (Nagauzura natane) were sowed and cultivated respectively in a greenhouse for 14 days. 500 ppm water suspensions of each of Compounds 1, 3, 5, 13, 14, 17, 20, 22, 24, 25, 26, 27, 28, 29, 31, 33, 34, 35, 37, 41, 54, 58, 63, 65, 68, 70, 71, 72, 79, 80, 96, 99, 102 and 105 made into formulations in the same manner as in Formulation example 1 were applied, respectively, by foliar application on the surfaces of the leaves of the kidney bean young seedlings in each of which the first leaf was developed, so that the water suspensions could sufficiently deposit thereon. After the chemical liquids were air dried, mycelial tuft discs of Sclerotinia sclerotiorum cultured on PDA medium were placed and thereby inoculated on the leaves respectively, the systems were held at 24° C. for 4 days under much moisture, and then the degrees of pathopoiesis were investigated. As a result, the pathopoiesis degree in the untreated section was 70%, whereas the pathopoiesis degrees in all the sections treated with the above compounds were under 5%.

As evident from the foregoing, the pyrazoline derivatives represented by the general formula 5 exhibit excellent control effects on plant diseases.

Biological test against powdery mildew of wheat (Seed treatment effect)

The formulated compounds according to the formulation example 4, 2, 3, 4, 5, 6, 7, 8, 9, 10, 12, 14, 15, 16, 18, 21, 22, 23, 25, 29, 30, 32, 33, 43, 49, 53, 55, 59, 66, 73, 77, 78, 79, 81, 85, 86, 89, 90, 91, 92, 96, 98, 101 and 102 were each sprayed onto the wheat seeds (Norin No. 73) by using a seed-dresser, wherein the applied amount of the compound was 400 g per 100 Kg of the seed. Then plastic cups of 130 ml were filled with sandy loam, to which the treated seed was sowed and kept in a greenhouse for 20 days. To the wheat seedings of the fourth leaf stage was sprayed a spore suspension of powdery mildew of wheat (Erysiphe graminis f. sp. tritici) to inoculate the seedling with the pathogen. After the inoculation, the infected seedlings were kept in a growth chamber at 15° C. for 10 days, and then the degrees of pathopoiesis were examined. The result showed that the degrees of pathopoiesis of untreated filed were 100%, while that of treated field using the above-described compounds showed 10% or less.

What is claimed is:

1. A method for controlling phytopathogenic fungi comprising applying a fungicidally effective amount of a plant disease-controlling composition containing as an effective ingredient a pyrazoline derivative represented by the general formula I

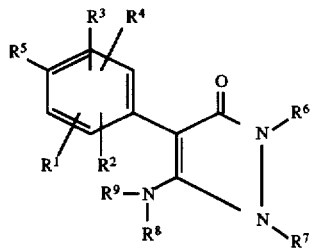

wherein $R^1$ to $R^4$ each denote a hydrogen atom, a halogen atom, an alkyl group, a haloalkyl group, an alkoxy group, an alkoxyalkoxy group, a haloalkoxy group, an alkylthio group, a haloalkylthlio group, a cyano group, a nitro group, an optionally substituted phenyl group or an optionally substituted phenoxy group, $R^5$ denotes a hydrogen atom, a fluorine atom or an alkoxy group, or adjacent two of $R^1$ to $R^5$ bind at each end to denote a group represented by CH=CH—CH=CH, a methylenedioxy group optionally substituted by halogen atom(s) or an alkylene group optionally containing one oxygen atom and optionally substituted by an alkyl group, one of $R^6$ and $R^7$ is a branched alkyl group and the other is an optionally substituted hydrocarbon group, and $R^8$ and $R^9$ are the same or different and each denote a hydrogen atom or an alkyl group, provided that not all of $R^1$ to $R^5$ denote hydrogen atoms at the same time.

2. The method of claim 1, wherein $R^6$ and $R^7$ are the same or different and each is selected from the group consisting of a tert-butyl group, an isopropyl group, a 1-methylbutyl group and a sec-butyl group, and wherein the fungicidally effective amount of the composition containing a pyrazoline derivative is applied to plant, soil or seed.

3. A method for controlling phytopathogenic fungi comprising applying a fungicidally effective amount of a plant disease-controlling composition containing a pyrazoline derivative represented by the general formula II

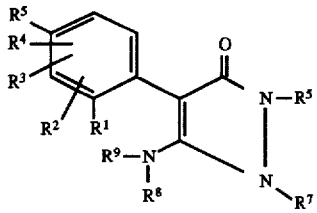

wherein, $R^1$ denotes a halogen atom, an alkyl group, a haloalkyl group, an alkoxy group, an alkoxyalkoxy group, a haloalkoxy group, an alkylthio group, a haloalkylthio group, a cyano group, a nitro group, an optionally substituted phenyl group or an optionally substituted phenoxy group.

$R^2$ to $R^4$ each denote a hydrogen atom, a halogen atom, an alkyl group a haloalkyl group, an alkoxy group, a haloalkoxy group, an alkylthio group, a haloalkylthio group, a cyano group, an optionally substituted phenyl group or an optionally substituted phenoxy group, $R^5$ denotes a hydrogen atom, a fluorine atom or an alkoxy group, one of $R^6$ and $R^7$ is a branched alkyl group and the other is an optionally substituted hydrocarbon group, and $R^8$ and $R^9$ are the same or different and each denote a hydrogen atom or an alkyl group, and wherein the fungicidally effective amount of the composition containing a proline derivative is applied to plant, soil or seed.

4. The method of claim 3, wherein $R^1$ is a halogen atom, a $C_1$ to $C_5$ alkyl group, a $C_1$ to $C_5$ haloalkyl group, a $C_1$ to $C_5$ alkoxy group, a ($C_1$ to $C_3$) alkoxy ($C_1$ to $C_3$) alkoxy group, a $C_1$ to $C_5$ haloalkoxy group, a $C_1$ to $C_5$ alkylthio group, a $C_1$ to $C_5$ haloalkylthio group, a cyano group, a nitro group, a phenyl group, (wherein the phenyl group may be substituted by halogen atom(s), $C_1$ to $C_5$ alkyl group(s), $C_1$ to $C_5$ alkoxy group(s), $C_1$ to $C_5$ alkylthio group(s), $C_1$ to $C_5$ haloalkyl group(s), $C_1$ to $C_5$ haloalkoxy group(s), $C_1$ to $C_5$ haloalkylthio group(s) or cyano group(s)), or a phenoxy group, (wherein the phenoxy group may be substituted by halogen atom(s), $C_1$ to $C_5$ alkyl group(s), $C_1$ to $C_5$ alkoxy group(s), $C_1$ to $C_5$ alkylthio group(s), $C_1$ to $C_5$ haloalkyl groups, $C_1$ to $C_5$ haloalkoxy group(s), $C_1$ to $C_5$ haloalkylthio groups) or cyano group(s)), $R^2$ and $R^4$ each are a hydrogen atom, a halogen atom, a $C_1$ to $C_5$ alkyl group, a $C_1$ to $C_5$ haloalkyl group, a $C_1$ to $C_5$ alkoxy group, a $C_1$ to $C_5$ haloalkoxy group, a $C_1$ to $C_5$ alkylthio group, a $C_1$ to $C_5$ haloalkylthio group, a cyano group, a phenyl group, (wherein the phenyl group may be substituted by halogen atom(s), $C_1$ to $C_5$ alkyl group(s), $C_1$ to $C_5$ alkoxy group(s), $C_1$ to $C_5$ alkylthio group(s), $C_1$ to $C_5$ haloalkyl group(s), $C_1$ to $C_5$ haloalkoxy group(s), $C_1$ to $C_5$ haloalkylthio group (s) or cyano group(s)), or a phenoxy group, (wherein the phenoxy group may be substituted by halogen atom(s), $C_1$ to $C_5$ alkyl group(s), $C_1$ to $C_5$ alkoxy group(s), $C_1$ to $C_5$ alkylthio group(s), $C_1$ to $C_5$ haloalkyl groups, $C_1$ to $C_5$ haloalkoxy group(s), $C_1$ to $C_5$ haloalkylthio group(s) or cyano group(s)).

$R^5$ is a hydrogen atom, a fluorine atom or a $C_1$ to $C_5$ alkoxy group, one of $R^6$ and $R^7$ is a branched alkyl group and the other is a $C_1$ to $C_{10}$ alkyl group, a $C_1$ to $C_{10}$ alkenyl group, a $C_2$ to $C_{10}$ alkynyl group, a $C_1$ to $C_{10}$ alkyl group substituted by the same or different 1 to 21 halogen atoms, a $C_2$ to $C_{10}$ alkenyl group substituted by the same of different 1 to 19 halogen atoms, a $C_2$ to $C_{10}$ alkynyl group substituted by the same or different 1 to 17 halogen atoms, a $C_1$ to $C_5$ alkoxy $C_1$ to $C_5$ alkyl group, a $C_1$ to $C_5$ alkylthio $C_1$ to $C_5$ alkyl group, a $C_1$ to $C_5$ alkyl group substituted by the same or different 1 to 11 halogen atoms and having a $C_1$ to $C_5$ alkylthio group substituted by the same or different 1 to 11 halogen atoms, a $C_1$ to $C_5$ alkyl group substituted by a cyano group, a $C_1$ to $C_5$ alkyl group substituted by a $C_1$ to $C_5$ alkoxycarbonyl group, a $C_3$ to $C_8$ cycloalkyl group, (wherein the cycloalkyl group may be substituted by halogen atom(s) or may contain unsaturated bond(s)), a phenyl group, (wherein the phenyl group may be substituted by halogen atom(s), $C_1$ to $C_5$ alkyl group(s), $C_1$ to $C_5$ alkoxy group(s), $C_1$ to $C_5$ alkylthio group(s), $C_1$ to $C_5$ haloalkyl group(s), $C_1$ to $C_5$ haloalkoxy group(s), $C_1$ to $C_5$ haloalkylthio group(s) or cyano group(s)), or a $C_7$ to $C_{17}$ aralkyl group, (wherein the aralkyl group may be substituted by halogen atom (s), $C_1$ to $C_5$ alkyl group(s), $C_1$ to $C_5$ alkoxy group(s), $C_1$ to $C_5$ haloalkoxy group(s), $C_1$ to $C_5$ haloalkylthio group(s) or cyano group(s)), and $R^8$ and $R^9$ are the same or different and each are a hydrogen atom or a $C_1$ to $C_5$ alkyl group, and wherein the fungicidally effective amount of the composition containing a pyrazoline derivative is applied to plant, soil or seed.

5. The method of claim 4, wherein all of $R^3$ to $R^5$ are hydrogen atoms, $R^2$ is a substituent at the 6-position and is a hydrogen atom, a halogen atom, a $C_1$ to $C_5$ alkyl group, a $C_1$ to $C_5$ haloalkyl group, a $C_1$ to $C_5$ alkyl group, a $C_1$ to $C_5$ haloalkyl group, a $C_1$ to $C_5$ alkoxy group, a $C_1$ to $C_5$ haloalkoxy group, a $C_1$ to $C_5$ alkylthio group, a $C_1$ to $C_5$ haloalkylthio group, a cyano group, a phenyl group, (wherein phenyl group may be substituted by halogen atom (s), $C_1$ to $C_5$ alkyl group(s) $C_1$ to $C_5$ alkoxy group(s), $C_1$ to $C_5$ alkylthio group(s), $C_1$ to $C_5$ haloalkyl group(s), $C_1$ to $C_5$ haloalkoxy group(s), $C_1$ to $C_5$ haloalkylthio group(s) or cyano group(s)), or a phenoxy group, (wherein the phenoxy group may be substituted by halogen atom(s), $C_1$ to $C_5$ alkoxy group(s), $C_1$ to $C_5$ alkylthio group(s), $C_1$ to $C_5$ haloalkyl group(s), $C_1$ to $C_5$ haloalkoxy group(s), $C_1$ to $C_5$ haloalkylthio group(s) or cyano group(s)), and wherein the fungicidally effective amount of the composition containing a pyrazoline derivative is applied to plant, soil or seed.

6. A method for controlling phytopathogenic fungi comprising applying a fungicidally effective amount of a plant disease-controlling composition containing a pyrazoline derivative represented by one of the following formulas

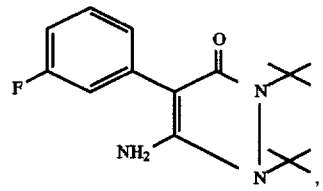

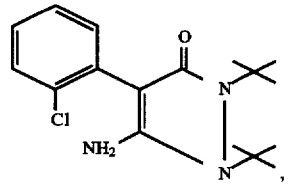

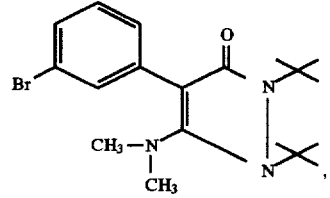

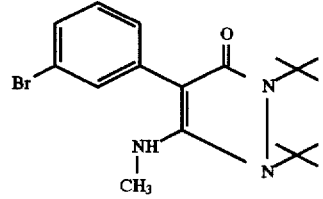

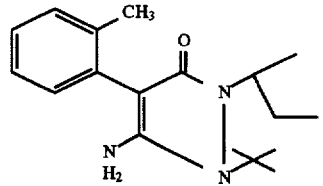

or

-continued
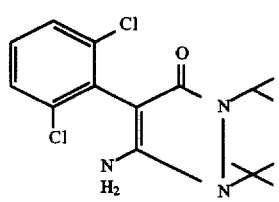
-continued
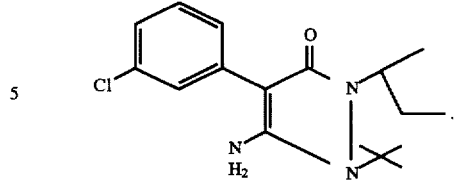
to plant, soil or seed.
* * * * *